(12) United States Patent
Nebolsin et al.

(10) Patent No.: US 7,759,313 B2
(45) Date of Patent: Jul. 20, 2010

(54) INDUCTION METHOD FOR CELL DIFFERENTIATION

(75) Inventors: Vladimir Evgenievich Nebolsin, Moscow (RU); Vera Andreevna Gorbunova, Moscow (RU); Ivan Dmitrievich Treschalin, Moscow (RU); Natan Tanfelevich Raikhlin, Moscow (RU); Avgust Mikhailovich Garin, Moscow (RU); Mark Borisovich Bychkov, Moscow (RU); Elena Mikhailovna Treschalina, Moscow (RU); Galina Alexandrovna Zheltukhina, Moscow (RU)

(73) Assignee: Obschetstvo S Ogranichennoi Otvetstvennostiyu "Pharmenterprises", Moscow (RU)

( * ) Notice: Subject to any disclaimer, the term of this patent is extended or adjusted under 35 U.S.C. 154(b) by 959 days.

(21) Appl. No.: 10/505,976

(22) PCT Filed: Feb. 28, 2003

(86) PCT No.: PCT/RU03/00072

§ 371 (c)(1),
(2), (4) Date: Apr. 6, 2005

(87) PCT Pub. No.: WO03/072124

PCT Pub. Date: Sep. 4, 2003

(65) Prior Publication Data

US 2005/0180953 A1 Aug. 18, 2005

(30) Foreign Application Priority Data

Feb. 28, 2002 (RU) .............................. 2002105392

(51) Int. Cl.
*A61K 38/00* (2006.01)
*C07D 233/61* (2006.01)

(52) U.S. Cl. .................. 514/19; 514/396; 548/335.5

(58) Field of Classification Search .................. 514/19, 514/396; 548/335.5
See application file for complete search history.

(56) References Cited

U.S. PATENT DOCUMENTS 5,350,836 A * 9/1994 Kopchick et al. ............ 530/399
6,838,436 B1 * 1/2005 Mundy et al. ................. 514/12

FOREIGN PATENT DOCUMENTS

| EP | 0271211 A2 | 8/1992 |
|---|---|---|
| EP | 1020179 | 12/2009 |
| GB | 2143732 A | 2/1985 |
| JP | A 60 16934 | 1/1985 |
| JP | A 64 42430 | 2/1989 |
| JP | A 5 85942 | 4/1993 |
| JP | A 7 309713 | 11/1995 |
| RU | 2141483 C | * 4/1997 |
| RU | 2141483 C1 | 11/1999 |
| WO | WO 95/11699 | 5/1995 |
| WO | WO 99/01103 | 7/1998 |
| WO | WO 99/24060 | 5/1999 |
| WO | WO 00/20576 | 4/2000 |

OTHER PUBLICATIONS

Ortiz et al in "Retinoids in combination therapies for the treatment of cancer: mechanisms and perspectives" [Drug Resistance Updates vol. 5 (2002) p. 162-175].*

Pouillart, "Role of Butyric Acid and its Derivatives in the Treatment of Colorectal Cancer and Hemoglobinopathies" [Life Sciences, vol. 63, No. 20, pp. 1739-1760, 1998].*

Francklyn et al., Aminoacyl-tRNA Synthetases: Versatile Players in the Changing Theater of Translation, RNA, vol. 8, pp. 1363-1372 (2002).*

Goodman & Gilman's The Pharmacological Basis of Therapeutics, 9th Ed., McGraw-Hill, NY, (1996).*

Nagase, H., et al., The Pharmacological Profile of δ Opioid Receptor Ligands, (+) and (−) TAN-67 on Pain Modulation, Life Sciences, vol. 68, pp. 2227-2231 (2001).*

Kick, E.K., et al., Structure-Based Design and Combinatorial Chemistry Yield Low Nanomolar Inhibitors of Cathepsin D, Chemistry & Biology, vol. 4, No. 4, pp. 297-307 (1997).*

Kulesz-Martin MF et al. "Differentiation and tumor response to retinobenzoic acid re-80 in a malignant conversion model"; Cancer Detect Prev, 1995; 19(4): 355-66.

Kuroki Toshio et al., (Iwanami Seminar) (Cell proliferation and cancer), 1999, p. 201-203.

Sibuya Masashi (Carcinogenic gene), Journal of clinical and experimental medicine, vol. 129, No. 13, p. 979 (1984).

Sakai Toshiyuki et al., Antitumor effect of prostaglandin D2 against a variety of human malignant tumor cell, Journal of clinical and experimental medicine, vol. 128, No. 5, p. 309-311 (1984).

Zhang et al., "Effect of polypeptide CH50 on macrophage activation in vivo anti tumor function", J Tongi Med Univ., 2000, 20(3), 190-3.

Lotan et al., "Stimulation of Melanogensis in a Human Melanoma Cell Lined by Retinoids", Cancer Research, vol. 40, Sep. 1980, p. 3345-3350.

Atzpodien et al., "Cancer, Cytokines, and Cytotoxic Cells: Interleukin-2 in the Immunotherapy of Human Neoplasms", Kiln Wochenschr, vol. 69, 1990, p. 1-11.

(Continued)

*Primary Examiner*—Rei-tsang Shiao
(74) *Attorney, Agent, or Firm*—Banner & Witcoff, Ltd.

(57) ABSTRACT

The invention relates to peptide derivatives which function as differentiation-inducing factors. The peptide derivatives are useful for treating cancer, particularly melanoma, for increasing the efficacy of melanoma immunotherapy, and for reducing hematological toxicity of chemotherapy.

20 Claims, No Drawings

OTHER PUBLICATIONS

Crawford et al., "Reduction by Granulocyte Colony-Stimulating Factor of Fever and Neutropenia Induced by Chemotherapy in Patients with Small-Cell Lung Cancer", The New England Journal of Medicine, Jul. 18, 1991, p. 164-170.

Kvamme et al., "N-Substituted Peptides in Brain", Proceedings of the Tenth FEBS Meeting, 1975, p. 127-136.

Abelev, "Differentiation and Tumor Phenotype in Cells of Leukemias and Lymphomas", A Handbook for Physicians: Clinical Oncohematology, 2001, p. 116-123.

Ichida et al., "Treatment of hepatitis B E-antigen-positive chronic hepatitis with a streptococcal preparation OK-432," DATABASE BIOSIS ABSTRACT of J. Int. Med. Res. 13, 59-67, 1985 (one page; downloaded and printed 2006).

Kaurov et al., "New gamma-L-glutamyl compounds useful as immunomodulatory compounds," Database WPI/DERWENT ABSTRACT of RU212098, 1997 (one page; downloaded and printed 2006).

* cited by examiner

INDUCTION METHOD FOR CELL DIFFERENTIATION

SPECIFICATION

The invention relates to medicine and in particular, to treating cancer diseases and it is useful in treating tumors of different origins.

The invention relates to a method for inducing cell differentiation using peptide derivatives as agents for inducing cell differentiation and, in particular, to their use in antitumor noncytotoxic therapy.

Absence of the ability to differentiate in most tumor cells is known to result in an uncontrollable tumor growth.

The search for agents of both specific and non-specific induction of cell differentiation is therefore one of novel approaches to anti-tumor noncytotoxic therapy.

Under "induction of cell differentiation" is included the capability of the different substances to restore (or to drive) the following functions, either lost or decreased because of various reasons: passing a normal cellular cycle by a cell, synthesis of biologically active vitally important substances therein etc.

Substances or compounds, the action mechanism of which is not associated with one particular cell function and that can cause its differentiation by several parameters, can be attributed to non-specific differentiation inducers.

Methods for inducing tumor cell differentiation by administering retinoids or α-2-interferon are known [Cancer Res., 40, 2245-3350, 1980].

The cell differentiation inducer polytransretinoic acid (PTRA) is used as an agent to prolong remission following induction or post-remission therapy of acute promyelocytic leukemia. Cell differentiation as affected by retinoic acid derivatives leads to stabilization of tumor cell growth [Abelev G. I. Differentiation and tumor phenotype in cells of leukosis and lymphomas/In: The Clinical Oncohematology (edited by M. A. Volkova). Moscow, the Meditsina publishers, 2001, Chapter 11, pages 116-123].

The use of α-interferon preparations as immunotherapy agents in treating melanoma is also associated with induction of tumor cell differentiation in which adhesion capability is enhanced and antigenic profile changes. Therapy with interferon results in reduced progression of tumor growth as well as prevention of the development and rate of metastasis [Atzpodien J., Kirchner H. Cancer, Cytokines, and cytotoxic cells: interleukin-2 in the immunotherapy of human neoplasms. Klin. Wochenschr, 1990, v. 68, pp. 1-7].

Preparations that cause hematopoietic cell differentiation of cells damaged due to cytotoxic the chemotherapy recently have been introduced into clinical practice. These preparations are different cytokines prepared from bone marrow, such as hematohormones: granulocytic colony-stimulating factor, granulocyte macrophage colony-stimulating factor and others. Their use in treating different human tumors results in accelerated maturation of the bone marrow cells and prevents hematologic cytotoxic effect of the chemotherapy preparations [Crawford j., Ozer H., Stoller R. et al. Phase II of clinical investigation of GM-CSF by the patients of SCLC with the dose-intensive the chemotherapy. The New England Journal of Medicine. 1991, v. 325, No. 3, pp. 164-170].

Thus, induction of tumor cell differentiation is one of the leading mechanisms of neoplasm growth stabilization, increased immunotherapy effect and correcting hematologic toxicity of the chemotherapy preparations.

The present inventors have discovered that peptide derivatives of general formula (I):

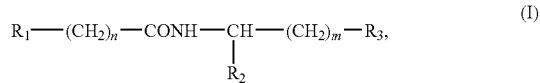

are potent inducers of cell differentiation and are useful as agents for non-cytotoxic therapy of Cancer diseases, in particular melanoma and hemoblastomas, as well as agents that affect hematopoiesis.

The compounds of formula (I)

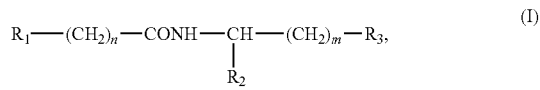

are disclosed in the International application PCT/RU98/00215 as possessing antioxidant, antiasthmatic, antihypoxic, anti-inflammatory, antiviral, antibacterial, lipid regulating, and anti-metastatic effects as well as other kinds of therapeutic effects. The compounds of cyclic aspartyl-histamine and acetyl-aspartyl-histamine structure are disclosed in the work Kvamme, E.; Reichelt, K. L.; Edminson, P. D.; et al. N-substituted peptides in brain. Fed. Eur. Biochem. Society Meet., {Proc.], 1975, 41, 127-136.

The present invention relates to a method for inducing cell differentiation comprising administration as an active agent of an effective amount of a compound of general formula

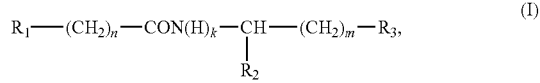

or pharmaceutically acceptable salts thereof, wherein $R_1$ is a $C_1$-$C_3$ hydrocarbon radical substituted by a functional group selected from amino, $C_1$-$C_5$ amido- or carboxylic groups, the carboxylic group being optionally etherified and the amino group being optionally substituted by an acyl substituent; or a $C_1$-$C_3$ hydrocarbon radical simultaneously substituted by an amino group, the amino group being optionally substituted by an acyl substituent and a carboxylic group, the carboxylic group being optionally included in a $C_5$-$C_6$ membered cyclic imide including an N-terminal amino group or an —NH— group of a —CONH— group; or a $C_1$-$C_3$ hydrocarbon radical substituted by a 5-6-membered unsaturated heterocyclic group, wherein the hydrocarbon radical can simultaneously comprise an amino group optionally substituted by an acyl substituent; or $R_1$ is a saturated heterocyclic group;

$R_2$ is a hydrogen atom or a functional group selected from carboxyl, that can be etherified;

$R_3$ is a 5-6-membered saturated or unsaturated cyclic or heterocyclic group, or an amino- or carboxyl group, the carboxyl group being optionally be etherified; and n=0-4, m=1-4, k=0-1.

In a preferred embodiment the present invention relates to a method for induction of cell differentiation comprising administration as an active agent of an effective amount of 4-[N-(2-imidazol-4-yl)ethyl)carbamoyl-]butyric acid (Dicarbamine®).

Preferred compounds of general formula (I) used in the present invention are compounds of general formula (I) shown below:

| Number of compound | R₁ | n | k | R₂ | m | R₃ |
|---|---|---|---|---|---|---|
| 1 | NH₂—CH(COOH)— | 2 | 1 | H | 1 | 4-Im (imidazole) (-4-Im) |
| 2 | HOOC—CH₂— | 2 | 1 | H | 1 | -4-Im |
| 3 | HOOC—CH₂— | 1 | 1 | H | 1 | -4-Im |
| 4 | NH₂—CH(COOH)— | 2 | 1 | —COOH | 1 | -4-Im |
| 5 | NH₂—CH(CH₂—CH₂—COOH)— | 0 | 1 | H | 1 | -4-Im |
| 6 | HOOC—CH₂— | 2 | 1 | —COOCH₃ | 1 | -4-Im |
| 7 | HOOC—CH₂— | 1 | 1 | —COOH | 1 | -4-Im |
| 8 | NH₂—CH₂— | 2 | 1 | —COOH | 1 | -4-Im |
| 9 | NH₂—CH₂— | 2 | 1 | —COOCH₃ | 1 | -4-Im |
| 10 | NH₂—CH₂— | 1 | 1 | —COOH | 1 | -4-Im |
| 11 | NH₂—CH₂— | 1 | 1 | H | 1 | -4-Im |
| 12 | NH₂—CH₂— | 2 | 1 | H | 1 | -4-Im |
| 13 | HOOC—CH₂— | 2 | 1 | —COOH | 1 | -4-Im |
| 14 | CH₃—CONH—CH(CH₂—COOH)— | 0 | 1 | H | 1 | -4-Im |
| 15 | R₁CON— = CH₃CONH—CH—C(=O)—N—C(=O)—CH₂ (succinimide) | 0 | 0 | H | 1 | -4-Im |
| 16 | R₁CON— = NH₂—CH—C(=O)—N—C(=O)—CH₂ (succinimide) | 0 | 0 | H | 1 | -4-Im |
| 17 | CH₃CONH—CH₂— | 2 | 1 | H | 1 | -4-Im |
| 18 | NH₂—CH(COOH)— | 1 | 1 | H | 1 | -4-Im |
| 19 | CH₃OCO—CH₂— | 2 | 1 | H | 1 | -4-Im |
| 20 | NH₂—CH(COOH)— | 2 | 1 | COOH | 1 | indole (-3-Ind) |
| 21 | NH₂—CH(CH₂—CH₂—COOH)— | 0 | 1 | H | 1 | -3-Ind |
| 22 | HOOC—CH₂— | 2 | 1 | —COOH | 1 | -3-Ind |
| 23 | NH₂—CH₂— | 2 | 1 | —COOH | 1 | -3-Ind |
| 24 | R₁CO— = pyroglutamyl (5-oxopyrrolidine-2-carbonyl) | 0 | 1 | H | 1 | -3-Ind |
| 25 | COOH—CH₂— | 2 | 1 | H | 1 | -3-Ind |

-continued

| Number of compound | R₁ | n | k | R₂ | m | R₃ |
|---|---|---|---|---|---|---|
| 26 | NH₂—CH(COOH)— | 2 | 1 | H | 1 | -3-Ind |
| 27 | NH₂—CH₂— | 2 | 1 | H | 1 | —C₆H₅ |
| 28 | NH₂—CH₂— | 2 | 1 | H | 1 | (—Py) |
| 29 | NH₂—CH(COOH)— | 2 | 1 | H | 1 | —Py |
| 30 | HOOC—CH₂— | 2 | 1 | H | 1 | —Py |
| 31 | HOOC—CH₂— | 2 | 1 | —COOH | 4 | —NH₂ |
| 32 | —NH₂—CH(CH₂—4Im)— | 0 | 1 | H | 1 | —COOH |
| 33 | R₁CO— = (pyrrolidine-NH-CO—) | 0 | 1 | H | 1 | -4-Im |
| 34 | HOOC—CH₂— | 2 | 1 | H | 1 | (morpholine) |
| 35 | —NH₂—CH(CH₂—4Im)— | 0 | 1 | H | 1 | —COOCH₃ |
| 36 | CH₃CO—NH—CH(COOH)— | 2 | 1 | H | 1 | -4-Im |
| 37 | CH₃CONH—CH₂— | 1 | 1 | —COOH | 1 | -4-Im |
| 38 | NH₂—CH₂— | 4 | 1 | H | 1 | -4-Im |

More preferred compounds of general formula (I) used in the present invention are compounds of general formula (I) wherein $R_1$=NH₂CH₂—, HOOC—CH₂—, CH₃CONH—CH₂—,

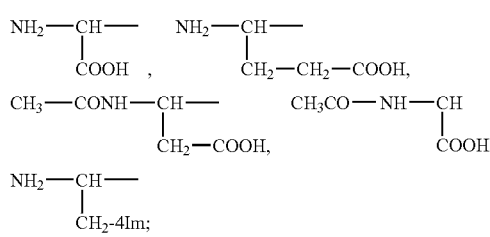

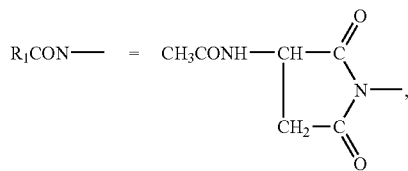

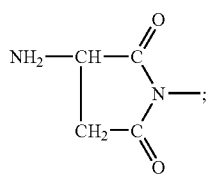

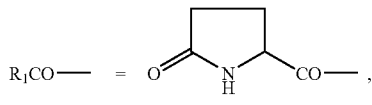

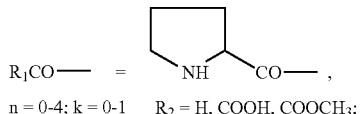

n = 0-4; k = 0-1    $R_2$ = H, COOH, COOCH₃;

$R_3$ = 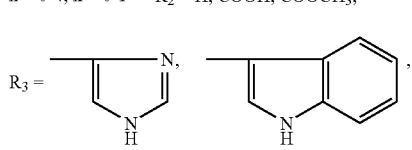

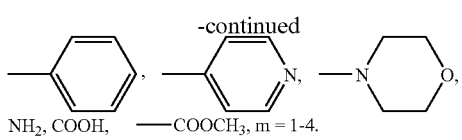

The most preferred compound used in the present invention is compound of the formula

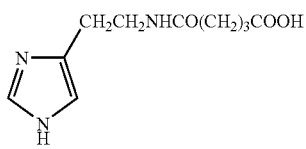

(Dicarbamine®).

In a preferred embodiment of the invention peptide derivatives of general formula (I) are administered for a long period of time at a single dose 0.5-5.0 mg/kg body weight.

In another preferred embodiment of the invention peptide derivatives of general formula (I) are administered in combination with the chemotherapy.

A preferred embodiment of the invention is also a method for induction of cell differentiation wherein in order to stabilize malignant tumors growth in particular melanoma or hemoblastosis, peptide derivatives of general formula (I) are administered at the single dose 0.5-5.0 mg/kg body weight for at least 15 days when the capabilities of the chemotherapy has been exhausted.

Administering peptide derivatives of general formula (I) in combination with the immunotherapy agent interferon results in enhancement of its efficacy in respect to malignant tumors cells in particular melanoma.

Yet another preferred embodiment of the present invention is a method for induction of cell differentiation wherein in order to enhance efficacy of melanoma immunotherapy, peptide derivatives of general formula (I) are administered at dose 0.5-5.0 mg/kg body weight for not less than 15 days together with administering interferon.

A preferred embodiment of the present invention is also a method for inducing cell differentiation wherein in order to lower hematological toxicity, peptide derivatives of general formula (I) are administered daily at the single dose 0.5-5.0 mg/kg body weight 5 days before starting a course of chemotherapy, during the chemotherapy, and within the period between a chemotherapy course and the next course of cytotoxic therapy.

Examples illustrating preferred embodiments of the instant invention are presented below.

EXAMPLE 1

Activity of Peptide Derivatives of General Formula (I) to Melanoma M-6 Cell Differentiation The study was conducted on 10-12 week old thymus free (nude) female Balb/C mice weighing 20-22 grams (breeding of the Russian Cancer Research Center (RCRC) named after N. N. Blokhin of the Russian Academy of Medical Sciences (RAMS)). A human melanoma strain earlier obtained from primary clinical material was taken from the bank of tumor strains of the RCRC of the RAMS for transplantation to thymus free "nude" mice. Tumor was disintegrated by Versen solution with vital Trypan blue staining and inoculated subcutaneously to mice in the amount of 1.6 million cells per mouse.

Dicarbamine was administered to mice intragastrically using a metal probe daily at dose 1.0 mg/kg beginning 4 days before the tumor inoculation and thereafter for 10-11 days (administration course up to 15 days). The mice were sacrificed with ether anesthesia in 12, 24 and 48 hours after the last administration.

Four groups of mice were used in the experiment:

Group 1—the control, no Dicarbamine is administered. Mice are sacrificed at the same times as those of the groups received Dicarbamine.

Group 2—Dicarbamine is administered and mice are sacrificed in 12 hours after termination of the administration.

Group 3—Dicarbamine is administered and mice are sacrificed in 24 hours after termination of the administration.

Group 4—Dicarbamine is administered and mice are sacrificed in 48 hours after termination of its administration.

Four morphologic parameters, such as the number of cells with pigment and the number of cells with apoptosis signs (capability to differentiate), the number of mitoses (proliferation activity), and necrosis area, were determined to monitor the degree of differentiation and proliferation of M-6 melanoma cells in the groups of control animals and in the Dicarbamine groups. These parameters were determined dynamically and correlated with general morphologic picture of a tumor growth as an integral sign. For this purpose, the tumors were removed from the mice, placed into formalin, and histologically processed for light microscopy. The data obtained are shown in Table 1.

TABLE 1

Morphologic parameters of M-6 melanoma (light microscopy)

| Parameters (in %) | | Time passed since Dicarbamine withdrawal | | |
|---|---|---|---|---|
| | | 12 hours | 24 hours | 48 hours |
| Necrosis area | Control | 1–2 | 2–3 | 3–5 |
| | Following Dicarbamine administration | 6–7 | 7–9 | 8–10 |
| Mitoses | Control | 3–5 | 3–5 | 3–5 |
| | Following Dicarbamine administration | 3–5 | 3–5 | 3–5 |
| Apoptosis | Control | 0.1–0.2 | 0.1–0.2 | 0.1–0.2 |
| | Following Dicarbamine administration | 0.1–0.2 | 0.2–0.3 | 0.2–0.3 |
| Cells with pigment | Control | 1–2 | 1–2 | 2–3 |
| | Following Dicarbamine administration | 2–3 | 2–4 | 3–5 |

The conducted study allowed the inventors to establish that human melanoma inoculated into nude mice at day 9 forms a tumor consisting of polymorph cells that grow by continuous fields with insignificant stromal development. Small necrosis sites are detected in the tumor, which sites slightly increase by 48 hours (up to 3-5% of slice area) as compared to time periods of 12 and 24 hours (1-2% and 2-3%, respectively). Three- to five-percent of mitoses are observed in the tumor during all growth periods. Apoptosis is slightly expressed. Cells containing pigment are rarely found; during the first day their number does not exceed 1-2%, and only during 48 hours of growth does it increase up to 2-3%. Thus, the intensity of melanin genesis during this period is insignificant. This information permits the conclusion that melanoma is a rapidly growing tumor which has practically lost its capability of differentiating on the basis of both the degree of apoptosis and first of all, on the basis of the basal functional capability of melanin genesis.

The effect of Dicarbamine on melanoma cell differentiation was assessed on the basis of the intensity of melanin genesis by counting the number of cells with melanin in the tumor slices. With this goal, tumors were excised from the mice, placed into glutaraldehyde and histologically processed for electronic microscopy. The Melanin Genesis Intensity Index (MGII), which reflects the degree of cell differentiation, was calculated in the prepared slices according to the following equation:

MGII=NCM×NM, wherein: NCM is the number of cells containing melanosomes;

NM is average number of melanosomes per a cell.

The analysis of melanin genesis intensity conducted by this index is shown in Table 2.

TABLE 2

Comparative melanin genesis intensity in melanoma cells following administration of Dicarbamine (electronic microscopy)

| Parameters (absolute values) | | Time passed since Dicarbamine withdrawal | | |
|---|---|---|---|---|
| | | 12 hours | 24 hours | 48 hours |
| Number of cells with melanosomes (per 500 cells) | Control | 135.0 | 144.0 | 159.0 |
| | Following Dicarbamine administration | 175.0 | 210.0 | 227.0 |
| Average amount of melanosomes per a cell | Control | 19.0 | 21.0 | 26.0 |
| | Following Dicarbamine administration | 28.0 | 35.0 | 42.0 |
| MGII | Control | 5.1 | 6.0 | 8.2 |
| | Following Dicarbamine administration | 9.8 | 14.7 | 19.0 |

*beginning from day 9 following the tumor inoculation

Electronic microscopy test shows that as compared to the control, the number of tumor cells comprising melanosomes and the number of melanosomes per one cell are increased due to an effect of Dicarbamine. The MGII index increases for the observed time periods as follows: in 12 hours—1.9-fold, in 24 hours—2.4-fold and in 48 hours—2.3-fold.

Thus, following a 15 day administration course of Dicarbamine, the average increase of M-6 melanoma tumor cell differentiation degree is 2.2-fold, which is supported by melanin genesis intensity (the MGII index), an increase in the number of cells comprising melanosomes (1.3-fold), and an increase in the number of melanosomes (1.3-fold).

EXAMPLE 2

The Effect of Dicarbamine on Melanin Synthesizing Function of Inoculated Human Melanoma Cells Mice with subcutaneously inoculated human melanoma as described in Example 1 were daily p.o. dosed with Dicarbamine at a higher single dose (4.5 mg/kg for 3 weeks from the moment of the tumor transplantation).

Animals were sacrificed three weeks after the tumor transplantation. By the time of sacrifice, the volume of the tumors was on average 150 mm$^3$. Following sacrifice, the tumors were excised from the mice and disintegrated with Versen solution, and the cell fraction containing cells with pigment was isolated. The number of cells with pigment was calculated in the Goryaev's chamber using light microscopy.

The conducted studies show that in the control mice the average number of cells with melanin was 39.14±8.75, and in the test mice it was 108.42±11.91, i.e. the number of cells synthesizing melanin significantly ($p<0.01$) increased by 3-fold.

Thus, in the conducted series of tests using Dicarbamine at the different doses, a statistically significant effect of pronounced induction of human melanoma cell differentiation was obtained as assessed on the basis of the melanin genesis intensity.

The data are presented in Table 3.

TABLE 3

Melanin genesis intensity in human melanoma cells induced by Dicarbamine

| | Control | | Test |
|---|---|---|---|
| Tumor number | Number of cells with melanin | Tumor number | Number of cells with melanin |
| 1 | 32 | 1 | 95 |
| 2 | 35 | 2 | 111 |
| 3 | 29 | 3 | 95 |
| 4 | 42 | 4 | 110 |
| 5 | 46 | 5 | 130 |
| 6 | 36 | 6 | 106 |
| 7 | 54 | 7 | 111 |
| Average | 39.14 | Average | 108.42* |
| Standard deviation | 8.72 | Standard deviation | 11.91 |

*$p < 0.01$

EXAMPLE 3

The Effect of Dicarbamine on Inoculated Human Melanoma Mel-6 Growth Dynamics

The study was conducted on 10-12 week old thymus free "nude" female Balb/C mice weighting 20-22 grams (breeding of the RCRC named after N. N. Blokhin of the RAMS). The human melanoma strain Mel-6 earlier obtained from primary clinical material was taken from the bank of tumor strains of the RCRC of the RAMS for transplantation to thymus free mice.

Dicarbamine at the single doses 1.5 mg/kg and 4.5 mg/kg was p.o. administered daily to two mice groups for 3 weeks from the moment of the tumor development (from day 15 to day 36 from the tumor transplantation).

Measurement of the tumor was done at days 18, 25, 33, 39, 46 and 53 from the transplantation. The effect of Dicarbamine was assessed on the basis of the tumor growth dynamics for 8 weeks in multiple measurements of tumor volumes "V" according to the formula:

$$V = \pi * L * s * h \text{ (mm}^3\text{)}$$

wherein L is length in mm, s is width in mm; and h is height in mm.

The ratio between volumes of tumors $V_t/V_f-1$ expressed as a percentage was then calculated and statistically processed according to the Student's method to calculate statistically significant difference. The data obtained are shown in Table 4.

The data obtained showed a 7-day delay in maximum tumor mass gain in comparison with the control. As compared with the control group, statistically significant differences in tumor growth rate were found at day 25 from the transplantation in the mouse group that received Dicarbamine at the single doses 4.5 mg/kg, which corresponds to a 10-day course of Dicarbamine dosing at a course dose 45 mg/kg. In this group the average tumor volume increased by 166.0±93.0%, whereas in the control group this parameter was 329.0±88.9% (p<0.015).

EXAMPLE 4

The Dicarbamine Effect in Combination with the Chemotherapy on the Growth of Inoculated Human M-6 Melanoma Transplanted to Thymus Free Mice The study was conducted according to the technique described in Example 3. Dicarbamine was administered daily p.o. at the single dose 4.5 mg/kg for 3 weeks from the moment of tumor appearance (from day 15 to day 36). In the groups of combined treatment Dicarbamine was also administered daily at the single dose 4.5 mg/kg for 3 weeks (days 15-36) in combination with a single administration of anti-tumor cytostatic agents Cysplatin at dose 6 mg/kg i.v. (day 25) and Aranoza at dose 40 mg/kg i.p. (day 27). Cytostatic therapy with was commenced when the average tumor volume reached 200±62 mm³. At days 18, 25, 33, 39, 46 and 53 from the transplantation tumor volumes were measured and the value $V_t/V_f-1$ was calculated and expressed as a percentage. The data obtained are shown in Table 5.

therapy scheme. Introduction of Dicarbamine into the inefficient chemotherapy scheme resulted in a statistically significant (p<0.05) decrease in the tumor mass gain at day 25 by 182.0±60.0%, which proves its efficacy in case of the absence of the chemotherapy effect.

EXAMPLE 5

The Effect of Peptides Derivatives of General Formula (I) on Proliferation Capability of Melanoma Cells when Interferon Administration The effect of Dicarbamine on proliferation capability of melanoma cells along with α-interferon (Introne®, IN) administration was studied. It should be noted that Dicarbamine itself is capable of slowing proliferation activity of melanoma cells without changing their survival.

The study was conducted on two continuous cell cultures growing in the form of a monolayer in a tissue culture (on murine B-16 melanoma cells and human M-5 melanoma cells). IN was administered at concentrations 70-700 IU/ml. Dicarbamine (D) was transferred into stock solution (1.000 μM), sterilized through filters with 0.22 μm pore diameter and then diluted to concentrations 0.01 and 1.0 μM.

The effect of preparations on cells was assessed on the basis of initial rate of cell proliferation (IRCP). This index (IRCP), which is usually called colony rate growth, was determined by numbering the number of cells in micro colonies during the first days following affection in "test" (with preparations) and "control" (without preparations) dishes, by analyzing 50 colonies in each of them. Each "point" included lesson fewer than three Petri dishes with growing cell colonies in adding specific concentrations of preparations under study. Growth rate of colonies (in %) was calculated according to the formula:

TABLE 5

The effect of combined the chemotherapy with anti-tumor cytostatic agents and Dicarbamine on human M-6 melanoma growth dynamics

| Mice group | Scheme of therapy Dose (mg/kg) single/course | Days of dosing | M ± m (%) at days after tumor inoculation | | | | |
|---|---|---|---|---|---|---|---|
| | | | 25 Day | 33 Day | 39 Day | 46 Day | 53 Day |
| Control | Physiological saline p.o. | 15–36 | 329.0 + 88.9 | 132.9 + 57.3 | 21.9 + 12.6 | 10.5 + 8.1 | 3.8 + 10.3 |
| Cysplatin | 6 mg/kg i.v. | 25 | 413.0 + 276.0 | 177.0 + 46.0 | 62.04 + 30.1 | 21.2 + 18.7 | 18.2 + 12.7 |
| Aranoza | 40 mg/kg i.p. | 27 | | | | | |
| Dicarbamine | 4.5/94.5 mg/kg p.o. | 15–36 | 166.0 + 93.0** | 276.0 + 104.0 | 39.8 + 27.3 | 19.6 + 17.5 | 4.2 + 22.5 |
| Dicarbamine | 4.5/94.5 mg/kg p.o.* | 15–36 | 182.0 + 60.0** | 191.0 + 71.0 | 24.5 + 17.4 | 28.7 + 9.8 | 8.0 + 30.6 |
| Cysplatin | 6 mg/kg i.v. | 25 | | | | | |
| Aranoza | 40 mg/kg i.p. | 27 | | | | | |

*daily;
**p < 0.05

It follows from the data presented that Dicarbamine in the used dosing route delays the tumor growth at initial stages, which can be shown by a decrease in tumor mass gain at day 25 166.0±93.0% as compared to the control, in which the gain was 329.0±88.9%. Thus the results of Dicarbamine effect on melanoma growth were reproduced (see Example 3). Combined the chemotherapy with Aranoza and Cysplatin in the indicated regimes appeared to be inefficient, i.e. gain of the tumor at this term was higher than the control value (413.0±276.0%). This proves the absence of sensitivity of the used Mel-6 human melanoma strain to the given the chemo- $$\frac{\text{Number of cells/colony (average value) in the test dishes} - 1}{\text{Number of cells/colony in the control dishes} - 1} \times 100\%$$

Cell numbers in micro colonies were calculated for every "point". Toxicity of preparations in the selected range of concentrations was judged by cell survival, which was determined by the ratio between numbers of the colonies grown in "test" and "control" dishes. Test results are shown in Table 6.

TABLE 6

The effect of Dicarbamine and α-interferon on proliferation activity of murine B-16 melanoma and human M-5 melanoma cells

| | | Initial rate of cell proliferation (% cells/colony relative to the control) at a term following contact with preparations | | | | | | | | |
|---|---|---|---|---|---|---|---|---|---|---|
| | | 48 hours | | | 72 hours | | | 96 hours | | |
| Preparation | IN concentration in IU/ml | Without D | D, 0.01 μM | D, 1.0 μM | Without D | D, 0.01 μM | D, 1.0 μM | Without D | D, 0.01 μM | D, 1.0 μM |
| Control of M-5 | | 100.0 | 84.2 | 69.0 | 100.0 | 73.6 | 50.0 | 100.0 | 70.2 | 49.1 |
| IN | 7.0 | 111.3 | 79.1 | 54.7 | 94.8 | 49.1 | 36.9 | 73.0 | 46.9 | 33.3 |
| | 70.0 | 53.7 | 40.5 | 30.7 | 51.9 | 34.9 | 24.5 | 48.8 | 31.7 | 23.9 |
| Control of B-16 | | 100.0 | 52.9 | 44.6 | 100.0 | 61.0 | 43.6 | — | — | — |
| IN | 70.0 | — | — | — | 50.2 | — | 26.1 | — | — | — |
| | 700.0 | 38.0 | 24.9 | 21.5 | 29.8 | 22.0 | 16.0 | | | |

One can see from the table that in the control with M-5 melanoma the IRCP index was preserved at the 100% level for 96 hours.

In the samples with M-5 cells when α-interferon was added at the concentration 7.0 IU/ml in 48 hours the IRCP index increased up to 111.3% and slowed down to 94.8 and 73.0%, respectively, only after 76 and 96 hours. When α-interferon was added at concentration 70 IU/ml in 48 hours, the IRCP index slowed down to 53.7%, in 72 hours—down to 51.9% and in 96 hours—down to 48.8%. That is, the maximum inhibiting effect of α-interferon at concentration 70 IU/ml achieves 50% IRCP.

When Dicarbamine at the concentration 0.01 μM was added, the IRCP index in 48 hours slowed down to 82.4%, in 72 hours—down to 73.6% and in 96 hours—down to 70.2%. When Dicarbamine at the concentration 1 μM was added, the IRCP index in 48 hours slowed down to 69.0% and in 72 hours—down to 50.0%.

Thus the maximum inhibiting effect of Dicarbamine also achieves 50% of the IRCP index and was obtained at the preparation concentration 1.0 μM.

In the tests on B-16 melanoma, when α-interferon was added at the concentration 70 IU/ml, the IRCP index in 72 hours slowed down to 50.0%, and when Dicarbamine was added at two indicated concentrations, the IRCP index in 48 hours slowed down to 52.9 and 44.6%, respectively, and in 72 hours to 61.0 and 44.6%, respectively. Significant reduction of the IRCP index down to 38.0 and 29.8% was obtained only when α-interferon was added at concentration 700 IU/ml.

Thus, the conducted tests show that α-interferon and Dicarbamine inhibit the growth of M-5 melanoma and B-16 melanoma cells at the level of 40.0-50.0%, which is characteristic of differentiation inducers. A more pronounced effect on the IRCP index can be obtained only in case of a 100-fold increase in α-interferon concentration.

Combined addition of α-interferon at concentration 70.0 IU/ml and Dicarbamine to M-5 cells shows that in all cases the IRCP index decreased to 30.7-24.0-31.0%, respectively, to recording terms. The most pronounced effect was obtained on B-16 melanoma when α-interferon at concentration 700 IU/ml and Dicarbamine at the both concentrations were used in combination: the IRCP index decreased to 24.9 and 29.8% in 48 hours and to 22.0 and 16.0% in 72 hours, respectively.

Thus, Dicarbamine similarly to α-interferon slows down murine B-16 melanoma and human M-5 melanoma cell proliferation and does not show toxicity (according to the survival index). As shown in the examples, the effect of Dicarbamine is characteristic of differentiation inducers and has an additive character in combination with the known differentiation inducer α-interferon on melanoma cells. This effect results in enhancement of tumor growth inhibition and it is an indication for raising immunotherapy efficacy for melanomas.

5.2. The Effect of Peptide Derivatives on the Proliferation Capability of Melanoma Cells The study was conducted on a continuous cell culture of murine B-16 melanoma growing in the form of a monolayer in a tissue culture. α-Interferon, selected as a preparation of comparison, was administered at concentration 70 IU/ml.

The tested compounds were transferred into stock solution (1,000 μM), sterilized through filers with 0.22 μm pore diameter and then diluted down to a concentration of 100 μM.

The effect of compounds on cells was assessed on the basis of initial rate of cell proliferation (IRCP). This index was determined by numbering the number of cells in micro colonies during the first days following affection in "test" (with preparations) and "control" (without preparations) dishes, by analyzing 50 colonies in each of them.

$$\frac{\text{Number of cells/colony (average value) in the test dishes} - 1}{\text{Number of cells/colony in the control dishes} - 1} \times 100\%$$

Calculations of cell numbers in micro colonies were done for every "point". Toxicity was judged by B-16 melanoma cell survival, which was determined by the ratio between numbers of the grown colonies in "test" and "control" dishes. Test results are shown in Table 7.

TABLE 7

The effect of peptide derivatives at concentration 100 μM and α-interferon at concentration 70 IU/ml on murine B-16 melanoma cells proliferative activity

| | Initial rate of cell proliferation (% cells/colony relative to the control) at a term following contact with preparations | |
|---|---|---|
| Compound | 48 hours | 72 hours |
| control | 2.52 = 100% | 3.49 = 100% |
| interferon | 29.6 + 2.3 | 27.4 ± 2.1 |
| dicarbamine | 30.8 ± 2.8 | 28.2 ± 2.2 |
| 1 | 26.6 ± 2.7 | 26.6 ± 2.8 |
| 2 | 25.5 ± 1.9 | 25.5 ± 1.7 |
| 3 | 35.6 + 2.9 | 35.6 ± 2.9 |

TABLE 7-continued

The effect of peptide derivatives at concentration 100 µM and α-interferon at concentration 70 IU/ml on murine B-16 melanoma cells proliferative activity Initial rate of cell proliferation (% cells/colony relative to the control) at a term following contact with preparations

| Compound | 48 hours | 72 hours |
|---|---|---|
| 4 | 38.3 ± 3.5 | 38.3 + 3.5 |
| 5 | 32.4 ± 2.6 | 32.4 ± 2.3 |
| 6 | 29.3 ± 2.4 | 29.3 + 2.2 |
| 7 | 38.8 + 2.7 | 38.8 ± 2.8 |
| 8 | 21.4 ± 1.5 | 16.9 ± 0.9 |
| 9 | 27.1 ± 1.7 | 17.2 ± 1.3 |
| 10 | 35.9 ± 3.6 | 23.1 ± 1.6 |
| 11 | 21.5 ± 1.9 | 20.7 ± 1.8 |
| 12 | 28.7 + 2.1 | 20.3 ± 1.9 |
| 13 | 44.9 ± 4.0 | 18.9 ± 1.4 |
| 14 | 33.8 ± 3.5 | 19.9 ± 1.8 |
| 15 | 39.7 + 2.5 | 29.8 + 2.3 |
| 16 | 41.3 ± 4.0 | 28.9 ± 2.5 |
| 17 | 39.7 ± 2.1 | 26.6 ± 2.1 |
| 18 | 42 ± 3 | 39 ± 3 |
| 19 | 21 ± 1 | 41 ± 5 |
| 20 | 44 + 3 | 42 + 4 |
| 21 | 42 ± 4 | 28 ± 2 |

Differences with the control are significant ($p<0.01$).

Data presented in Table 7 show that peptide derivatives inhibit B-16 melanoma cell colonies growth at the level 50.0-70.0% that is characteristic of differentiation inducers.

EXAMPLE 6

Distribution of Tumor Cells by Cell Cycle Phases at Different Times Following Dicarbamine Administration Tests were done on inoculated B-16 melanoma. The effect of Dicarbamine on the distribution of tumor cells was studied on the basis of DNA content at different times following administration of the preparation. From day 6 after the tumor inoculation mice for 10 days were daily intragastrically given with 0.5 mg/kg Dicarbamine. Animals were sacrificed with subsequent investigation of tumor material at days 10, 12, 16 and 18 after inoculation, i.e. days 5 and 7 respectively after Dicarbamine administration as well as in 2 and 4 days after termination of Dicarbamine 10-day dosing.

Test results shows that Dicarbamine caused a significant increase of the portion of interphase tumor cells ($IIG^1$) (≈25%). In a constant portion of proliferating cells (≈30%) increase in the portion of $IIG^2$ cells (12-14%) is noted. Accordingly the portion of normal stromal cells ($IG^1$) in the samples compensatory decrease. Said changes are most clearly pronounced after 5-10 administrations of Dicarbamine.

Course dosing of Dicarbamine causes kinetic rearrangement of tumor cell populations. Inhibition of cells in the synthetic cycle phase (S-phase) is noted with compensatory decrease in the portion of cells that are ready for proliferation or proliferating cells ($G^2$ phase). Accumulation of tumor cells in the stationary phase $G^1$ simultaneously occurs.

Lowering the level of proliferative activity Dicarbamine promotes accumulation of cells in stationary (non-proliferating) cell cycle phase. It can slow down tumor growth and promote transition of cells to a more differentiated state.

EXAMPLE 7

Efficacy of Dicarbamine in Respect to Hematological Toxicity of Cyclophosphamide and its Combinations with Cysplatin and Carboplatin The effect of Dicarbamine on hematopoiesis was studied on the first generation of male mice hybrids F, (CBA×$C_{57}$BI).

7.1. 4 Groups of animals were used to study the effect of Dicarbamine on hematotoxicity of Cyclophosphamide (CPH):

Group 1—Dicarbamine, 0.5 mg/kg daily beginning 5 days before CPH administration and for 5 days after the single administration of CPH at dose 200 mg/kg;

Group 2—the single administration of 200 mg/kg CPH;

Group 3—intact control;

Group 4—Dicarbamine 0.5 mg/kg daily for 10 days.

The data obtained are shown in Table 8.

TABLE 8

Total leukocyte number in peripheral mice blood under Cyclophosphamide effect and Cyclophosphamide with Dicarbamine Total leukocyte number (in thousand in mm$^3$) at days post Cyclophosphamide dosing

| Group | 3 | 5 | 7 | 10 | 13 | 17 | 21 |
|---|---|---|---|---|---|---|---|
| 1 | 2.80 ± 0.22 | 7.96 ± 1.10 | 13.38 ± 1.54 | 11.88 ± 1.92 | 13.30 ± 1.48 | 12.40 ± 1.76 | 12.90 ± 2.60 |
| 2 | 1.06 ± 0.44 | 4.38 ± 0.77 | 10.50 ± 3.02 | 6.44 ± 0.60 | 12.20 ± 3.02 | 12.20 ± 1.80 | 11.86 ± 1.32 |
| 3 | 16.50 ± 8.20 | 16.10 ± 3.20 | 14.80 ± 3.30 | 15.80 ± 1.90 | 14.90 ± 2.70 | 16.90 ± 4.70 | 14.70 ± 2.80 |
| 4 | 15.70 ± 4.30 | 15.30 ± 7.80 | 17.30 ± 5.10 | 15.70 ± 3.80 | 12.50 ± 3.52 | 17.80 ± 4.70 | 16.30 ± 3.90 |

The data obtained show that use of Dicarbamine in combination with CPH results in a reduced hematotoxic effect of the latter and an increased recovery of blood parameters.

7.2. When studying the effect of Dicarbamine on hematotoxic action of CPH combinations with platinum derivatives, Dicarbamine was intragastrically administered to mice for 20 days daily at a single dose of 0.5 mg/kg. Cytostatic preparations were administered once intraperitoneally at day five after starting the Dicarbamine administration course. Doses of cytostatic preparations are shown in Tables 10 and 11.

The results of studying the effect of Dicarbamine on leukocyte number in mouse peripheral blood when combined dosing of CPOH with Cysplatin or Carboplatin are shown in Tables 9 and 10 respectively.

The data presented show (Table 10) that when Dicarbamine is used together with Carboplatin and Cyclophosphane at the lethal doses, leukocyte number in peripheral blood and times of animals death are similar to the data presented in Table 9.

TABLE 9

The effect of Dicarbamine on hematotoxicity of Cyclophosphamide in combination with Cysplatin

| Cytostatic preparation | Cdtistatic preparation dose(mg/kg) | Total leukocyte number (in thousand in mm$^3$) at days after cytostatic preparations dosing | | | | | Terms of death (days) |
|---|---|---|---|---|---|---|---|
| | | 0 | 3 | 5 | 7 | 21 | |
| Dicarbamine CPH Cysplatin | 200 8 | 11.30 ± 2.30 | 2.32 ± 0.49 | 6.60 ± 0.90 | 10.40 ± 1.54 | 12.30 ± 1.56 | 8; 16 |
| CPH Cysplatin | 200 8 | 11.30 ± 2.30 | 1.20 ± 0.33 | 4.32 ± 0.77 | 6.24 ± 1.15 | 10.80 ± 1.02 | 3; 4; 7 |
| Dicarbamine CPH Cysplatin | 100 4 | 11.30 ± 2.30 | 4.14 ± 0.60 | 11.40 ± 1.10 | 14.90 ± 1.32 | 11.80 ± 1.32 | no |
| CPH Cysplatin | 100 4 | 11.3 ± 2.3 | 2.65 ± 0.66 | 4.74 ± 0.66 | 8.05 ± 0.88 | 12.0 ± 1.4 | no |
| Dicarbamine CPH Cysplatin | 50 2 | 11.30 ± 2.30 | 6.70 ± 1.15 | 17.00 ± 5.17 | 14.50 ± 2.00 | 12.40 ± 0.99 | no |
| CPH Cysplatin | 50 2 | 11.30 ± 2.30 | 4.04 ± 0.77 | 7.62 ± 0.99 | 8.72 ± 1.15 | 13.10 ± 1.54 | no |

The presented data show that already by day 5 in the mouse group that received cytostatic preparations at maximal doses along with Dicarbamine, leukocyte number achieved lower border of physiological norm and by day 7 it was nearly restored to its the initial level. Without Dicarbamine, restoration was observed only by day 21 of the test. In mice that received cytostatic preparations at maximum doses without Dicarbamine, death of the animals was noted at days 3, 4 and 7 of the test. In animals that were given cytostatic preparations at maximum doses along with Dicarbamine, only delayed death at days 8 and 16 was noted.

Thus, Dicarbamine inhibits the development of leukopenia in all the courses studied, it speeds up recovery of total leukocyte number, and delays the time of death in mice when using cytostatic preparations at lethal doses.

7.3. When studying the effect of peptide derivatives of general formula (I) on hematotoxic action of CPH combinations with Carboplatin, the compounds were intragastrically administered to mice daily at the dose 0.5 mg/kg for 10 days. At day five after starting administration of the tested compounds, mice were intraperitoneally injected with CPH at dose 200 mg/kg and with Carboplatin at a single dose 15

TABLE 10

The effect of Dicarbamine on hematotoxicity of Cyclophosphamide in combination with Carboplatin

| Cytostatic preparation | Cytostatic preparation dose(mg/kg) | Total leukocyte number (in thousand in mm$^3$) at days after cytostatic preparations dosing | | | | | Terms of death |
|---|---|---|---|---|---|---|---|
| | | 0 | 3 | 5 | 7 | 21 | |
| Dicarbamine CPH Cysplatin | 200 30 | 11.50 ± 2.80 | 3.10 ± 0.70 | 12.80 ± 1.37 | 15.30 ± 1.26 | 12.30 ± 0.89 | 10 |
| CPH Cysplatin | 200 30 | 11.30 ± 2.30 | 1.18 ± 0.49 | 4.60 ± 0.60 | 7.54 ± 0.77 | 12.60 ± 1.28 | 3 |
| Dicarbamine CPH Cysplatin | 100 15 | 11.50 ± 2.80 | 4.04 ± 0.44 | 10.40 ± 1.59 | 14.80 ± 1.76 | 11.80 ± 1.34 | no |
| CPH Cysplatin | 100 15 | 11.30 ± 2.30 | 2.74 ± 0.49 | 6.48 ± 0.60 | 10.50 ± 1.38 | 13.20 ± 1.50 | no |
| Dicarbamine CPH Cysplatin | 50 7.5 | 11.30 ± 2.30 | 6.60 ± 0.77 | 10.90 ± 1.21 | 11.20 ± 1.20 | 10.90 ± 1.28 | no |
| CPH Cysplatin | 50 2 | 11.50 ± 2.80 | 3.94 ± 1.04 | 8.72 ± 1.98 | 10.80 ± 2.40 | 11.20 ± 0.99 | no | mg/kg. Thereafter, administration of the tested compounds was continued for 5 more days.

Before starting the dosing of the tested compounds, blood was drawn from the tail to calculate total leukocyte number. At days 3, 5 and 7 after administration of Cyclophosphamide with Carboplatin, blood also was drawn from the tail to calculate total leukocyte number. Each group included 15 animals.

As a control a mouse group that received only cytostatic preparations was used.

The data presented in Table 11 show that peptide derivatives of general formula (I) inhibit the development of leukocytopenia and speed up recovering total leukocyte number.

A strain of Friend erythroblastosis was obtained from the bank of tumor strains of the GU RCRC named after N. N. Blokhin of the RAMS. It was twice passaged intraperitoneally using generations 3-8 in subcutaneous inoculation. The inoculation was done using a cellular suspension of $1 \times 10^6$ cells in 0.3 ml 1999 medium.

Solutions of the tested compounds were intra-gastrically daily administered to mice using a probe from day 3 to day 7 after tumor inoculation.

Therapeutic efficacy was assessed on the basis of tumor growth inhibition (TGI, %) and an average life span (ALS). Increase in life span was determined by the commonly accepted criterion T/C (%), which was calculated as a ratio

TABLE 11

The effect of peptide derivatives of general formula (I) on hematotoxic action of Cyclophosphamide combination with Carboplatin

| No. of compound | Total leukocyte number in peripheral blood (in thousand in mm$^3$) at days after dosing of cytostatic preparations | | | |
|---|---|---|---|---|
| | 0 | 3 | 5 | 7 |
| 1 | 13.3 ± 3.5 | 3.3 ± 1.0* | 10.0 ± 1.3* | 11.6 ± 2.5* |
| 2 | 13.8 ± 3.5 | 3.18 ± 0.82* | 9.1 ± 0.5* | 11.9 ± 2.5* |
| 3 | 15.5 ± 3.2 | 4.18 ± 2.0 | 19.2 ± 1.9 | 17.5 ± 1.7* |
| 4 | 15.3 ± 2.7 | 3.02 ± 0.83 | 9.62 ± 3.84 | 16.1 ± 0.15 |
| 5 | 12.1 ± 1.4 | 2.1 ± 1.04 | 10.5 ± 2.08 | 15.26 ± 1.23 |
| 6 | 14.2 + 1.1 | 3.04 + 1.61 | 14.56 + 2.65 | 25.68 + 3.1* |
| 7 | 13.7 ± 1.1 | 3.14 ± 0.62 | 13.7 ± 0.57 | 16.58 + 2.9 |
| 8 | 12.9 + 2.5 | 3.98 ± 0.78 | 10.8 ± 0.57 | 16.16 ± 0.85 |
| 9 | 13.2 ± 3.0 | 5.04 + 0.20* | 8.64 ± 1.97 | 19.38 + 1.8 |
| 10 | 12.9 ± 1.9 | 5.18 ± 1.97* | 19.76 ± 3.22* | 21.82 ± 3.74* |
| 11 | 14.8 ± 2.3 | 3.32 ± 1.3 | 10.28 ± 1.35 | 17.56 + 2.6 |
| 12 | 12.8 ± 0.8 | 3.56 ± 0.12 | 20.66 ± 3.7* | 17.4 + 2.8 |
| 13 | 14.9 ± 0.6 | 2.66 ± 0.21 | 25.7 ± 4.1* | 32.1 ± 4.87* |
| 14 | 13.8 ± 0.5 | 2.66 ± 0.23 | 16.24 + 2.3 | 28.9 ± 3.65* |
| 15 | 12.7 ± 0.7 | 3.76 ± 0.14 | 26.4 ± 5.8* | 27.6 ± 4.12* |
| 16 | 12.6 ± 0.6 | 3.9 ± 0.23 | 15.44 ± 1.3 | 24.9 ± 4.31* |
| 17 | 13.4 ± 0.8 | 3.36 ± 0.27 | 17.6 ± 3.1 | 26.1 ± 3.97* |
| CPH + C | 16.1 ± 3.5 | 1.14 ± 0.55 | 4.31 ± 1.3 | 8.3 ± 0.58 |

*significant at $p \leq 0.05$ 7.4. The effect of Dicarbamine on cell differentiation is supported by the study of mouse peripheral blood differential number under Cyclophosphamide effect in combination with Dicarbamine in comparison with dosing Cyclophosphamide alone.

Two groups of mice are used. Group one is administered Dicarbamine at dose 0.5 mg/kg 5 days prior to and 5 days after CPH administration at dose 200 mg/kg. Group two of mice is administered CPH alone at dose 200 mg/kg. Results of the studies are shown in Tables 12 and 13.

Data presented in Tables 12 and 13 show that recovering peripheral blood occurs due to burst of mature forms, which confirms the differentiation effect of Dicarbamine. This is especially seen at days 3 and 5 by peripheral blood number and cellularity of bone marrow (Tables 12 and 13). In the group with Dicarbamine, myelocytes and band neutrophils are absent in peripheral blood and in group without Dicarbamine these form elements are present (Table 12).

EXAMPLE 8

Decrease in the Rate of and Dimensions of Subcutaneously Inoculated Friend Erythroblastosis (FEB) in Mice as Effected by Peptide Derivatives The studies were conducted on male mice hybrid 100 $BDF_1$ that were divided into groups containing 10 mice each. Lineal $DBA_2$ mice were used for passaging FEB in vivo.

between ALS in the test and control groups. Tumor growth rate $V_t/V_1$ was calculated on the basis of change growth in average tumor volumes.

Data from the studies of the effect of peptide derivatives on tumor size and on tumor growth rate are shown in Tables 14 and 15, respectively.

The results obtained show that peptide derivatives cause growth inhibition of subcutaneously inoculated FEB for 19 days after termination of therapy. Said effect started to be recorded immediately after termination of administering compounds at a single dose 1.5 mg/kg and was preserved at a significant level (p<0.05) up to day 13. Tumor growth rate was stabilized during one week following withdrawal of the compounds.

It was established resulting from the conducted studies that the compounds of general formula (I) possess an inhibiting effect on the development of FEB subcutaneous nodes. The data obtained suggest that the test compounds are useful for therapy of human hemoblastoses.

EXAMPLE 9

The Effect of Dicarbamine and 2α-Interferon (Reaferon) on Friend Erythroblastosis Tumor Cells Friend erythroblastosis which was inoculated subcutaneously to $DBA_2$ female mice via spleen cells was investigated.

4 groups of tests were carried out.

Group 1—control animals without therapy, a physiological saline was administered;

Group 2—Reaferon at dose 100 thousand IU/kg was administered daily s.c. from day 3 to day 7 after inoculation;

Group 3—Dicarbamine at a single dose 4.5 mg/kg was administered p.o. from day 3 to day 7 after inoculation;

Group 4—Dicarbamine and Reaferon were administered simultaneously according to a similar scheme.

Material for light microscopy was taken from sacrificed animals at days 3, 7 and 14 after termination of therapy or administration of a physiological saline. Material for electronic microscopy was taken at days 7 and 14.

For histological examination, tumor pieces were fixed in 10% neutral formalin and imbedded into paraffin; slices obtained were stained with hematoxylin-eosin and examined for glycogen (polysaccharide) content using the periodic acid Schiff reaction, for RNA content according to Brachet, and for lipids and iron. Slices were examined and photographed using a Polivar light microscope (Austria).

For electronic microscopy, tumor pieces were fixed in a 2.5% glutaraldehyde solution and 1% osmium tetroxide and embedded in EPON-812. Semi-thin and ultra-thin slices were prepared on the LKB-III ultratome (Sweden). The obtained semi-thin slices were stained with Toluidine blue and examined through the light microscope. Ultra-thin slices were additionally stained with uranyl acetate and lead citrate; the slices examined and photographed in the JEOL 1200 EX-II electronic microscope (Japan).

The percentage of cells with different types of differentiation (blast cells, lymphocytes and granular leukocytes) was calculated during electronic microscopy for quantitative assessment.

The percentage of mitoses and cells with apoptosis, as well as areas of necrosis, were assessed during histological examination.

Histological Examination

Group 1. Control Animals without Therapy

It was found at histological examination that tumor cells are large and polymorphous, their nuclei are light, and their cytoplasm is moderately developed. Cellular size sometimes fluctuates, and individual smaller cells are present, but large cells represent the main mass of cells.

Tumor cells form continuous outgrowths. In individual tumors, necrosis sites surrounding preserved fields of tumor cells are present. Area of necroses did not exceed 10-15% of the slice surface.

In a majority of tumor cells, the Brachet reaction for RNA is strongly pronounced, less often it is weak or absent (in individual small cells).

The periodic acid Schiff reaction was diffuse in character, and iron was detected only in individual cells.

In the tumor, among large cells mitoses were detected (up to 1-1.5%) and signs of apoptosis were detected (up to 0.5%).

As the tumor grew, the area of necroses increased up to 20-30% of the slice surface, the number of mitoses increased (up to 1.5-2%), and apoptosis activity did not change. The number of large polymorphous cells significantly prevailed at all times.

Group II. Administration of Reaferon

Tumors have usual histological structure. As in the control, among large polymorphous cells smaller cells with hyperchromatic nucleus are found.

By day 14 the area of necrosis is 40-50% of the slice surface and mitotic activity is 0.5-1%. By day 7 apoptosis increased up to 1-2%, but by day 14 it decreased to 1-1.5%.

Group III. Administration of Dicarbamine

Increase in the quantity of small tumor cells with hyperchromatic nuclei is noted. Quantity of large polymorphous cells significantly prevails. The area of necrosis did not significantly change as compared to the picture in group I. Mitotic activity also remained within the limits of the control figures. At days 3 and 7 the rate of apoptosis slightly decreased (down to 0.1=0.5% at day 7).

Group IV. Simultaneous Administration of Dicarbamine and Reaferon

The area of necrosis and mitotic activity did not show significant shifts as compared to the changes in group II. At day 3, apoptosis decreased to 0.2-0.5%, at days 7 and 14 it is 0.5% (as in the control).

Large polymorphous cells of blast type significantly prevail in the tumor.

Electronic Microscopy

Group 1. Control Animals without Treatment

Large polymorphous low-differentiated cells of blast type are mainly found in the tumor during electronic microscopy. Nuclei in these cells have rounded or a slightly irregular shape, occasionally with an uneven surface. Diffuse distribution of chromatin is usually seen in them, and only in some of them is the formation of marginally located heterochromatin noted. Nuclei usually occupy a major portion of cytoplasm, where ribosomes, single mitochondria, and, occasionally, the structures of slightly rough endoplasmic reticulum prevail. Blast cells amount 90-95% of all the tumor population.

In addition to blast cells, lymphocytes of different maturity degree are observed, i.e. lymphoblasts, lymphocytes (large, medium, small). Nuclei in these cells are rounded, oval, often with an uneven surface, and they comprise heterochromatin in the form of large accumulations. Nucleoli are observed. Cytoplasm is moderately developed and comprises many ribosomes; there are few other organelles. Dense granules are occasionally observed.

Granular leukocytes are small, granules characteristic of neutrophils, less often eosinophils are visible in cytoplasm. Nuclei in cells are segmented or have deep concavities. Cells having granules in cytoplasm, an irregular nucleus, and protruding plasma membrane in the form of processes can be occasionally seen (monocytes). Freely lying red blood cells were observed in the tumor.

Large blast cells mainly prevail in the tumor (up to 90-95%). Lymphoid cells are observed within the range of 4-8%, and granular cells amount 1-2%.

No significant shifts in the ratio between different cell types were noted as the tumor grew following engrafting.

Group II. Administration of Reaferon

General ultrastructure of tumor cells of different type is preserved.

Quantity of large blast cells does not decrease, and lymphoid cells amount up to 4-8%, granular leukocytes amount up to 1-2%. Individual red blood cells are present in the tumor.

Group III. Administration of Dicarbamine

Ultrastructure of tumor cells of different type remains previous. Their quantitative ratio changes and differentiation level somewhat increases. The quantity of large blast type cells decreases to 70-80%, the quantity of lymphocytes and granulocytes increases up to 18-25% and 2-5%, respectively. Individual red blood cells are present in the tumor.

The most constantly found changes are observed at day 7 post-treatment.

Group IV. Administration of Reaferon and Dicarbamine

Ultrastructure of tumor cells of different type practically corresponds to what is described above (see Group I).

The quantity of large blast type cells fluctuates within the range of 70-80%. The number of lymphocytes achieves 18-25%, the quantity of leukocytes remains at the level of 2-5%. Red blood cells are observed among the other cells.

As in the previous groups, the changes found are most pronounced at day 7.

Thus, Dicarbamine orally administered to mice with Friend erythroblastosis at a dose of 4.5 mg/kg daily for 5 days was demonstrated to cause differentiation of immature tumor cells mainly in the direction of forming granulocytes as well as cells of erythroid lineage.

As compared to tumors of the control animals, when Dicarbamine was used the quantity of immature tumor cells decreased from 90-95% to 70-80%, i.e. by 15-20%, and the quantity of lymphocytes increased from 4-8% up to 18-25%, i.e. 4-fold.

The quantity of granulocyte lineage cells increased less significantly (from 1-2% to about 2-5%).

It should be noted that most frequently changes were found at day 7 after the termination of treatment. At day 14 after termination of treatment these changes were stabilized.

Reaferon in subcutaneous administration for 5 days at dose 100 thousand IU/kg caused increase in the area of necrosis in the tumor (from 15-20% in the control to 40-50% in the test at day 7 after termination of treatment and from 20-30% to 40-50% at day 14). The rate of mitoses somewhat decreased (from 1.5-2% to 0.5-1%), and the number of cells with signs of apoptosis increased (from 0.5% to 1-2% at day 7 after termination of treatment). Differentiation of tumor cells did not practically change.

In simultaneous administration of Dicarbamine and Reaferon at the same doses and at the same times summation of the effect of each preparation was found. Enhancement of differentiation of blast immature cells characteristic of the effect of Dicarbamine alone was observed as well as growing area of necrosis, and a decrease in the number of mitoses were found that was seen in administering Reaferon alone.

Thus, it has been established that Dicarbamine is capable of enhancing differentiation of immature tumor hematopoietic cells of Friend erythroblastosis in different directions, in particular in formation of lymphoid and myeloid lineage tumor cells.

The effect of Dicarbamine on cell differentiation represents its general property, as observed in the melanoma study, above.

EXAMPLE 10

Electronic Microscopy of Dicarbamine Protective Effect with Respect to Hematopoietic Cells of the Bone Marrow and Peripheral Blood in Patients with Ovarian Cancers During the Chemotherapy In the previous studies devoted to studying the mechanism of action of Dicarbamine on the bone marrow, the given preparation was found to protect the bone marrow in animals under test conditions against adverse cytotoxic effect of Cyclophosphamide by reducing apoptosis in normal hematopoietic cells.

Similar data were obtained on the bone marrow puncture biopsies and peripheral blood of 10 patients with stage III-IV ovarian cancer.

The patients were divided into two equal groups: group I—patients who received the chemotherapy alone and group II—patients who received the chemotherapy along with Dicarbamine administration.

Patients in groups I and II received 600 mg/m$^2$ Cyclophosphane and 400 mg/m$^2$ Carboplatin during the first day of therapy; courses were repeated with a 3-4 week interval. The average chemotherapy course of one patient included 6 courses without Dicarbamine and 5.7 courses with Dicarbamine.

In group II patients received the chemotherapy along with Dicarbamine dosing at a single dose 100 mg beginning 5 days before the first course and then until the beginning of next course at the same dose. Duration of Dicarbamine use between two courses averaged 24.5 days. Average total dose was 2.5 grams.

Puncture biopsy of the bone marrow and peripheral blood for electronic microscopy were taken from patients prior to the chemotherapy and at the end of treatment course with Dicarbamine or without it.

Fresh bone marrow puncture biopsies were placed on a slide plate and stirred many times with a stirring rod until small dense fragments were obtained. The latter were fixed in a 2.5% glutaraldehyde solution and additionally fixed in a 1% osmium tetroxide solution; following washing with phosphate buffer at pH 7.4, they were dehydrated in alcohols of increasing concentration and embedded in the mixture of epoxy resins EPON-812. Semi-thin and ultra-thin slices were prepared on the LKB-III ultratome (Sweden). The semi-thin slices were stained with Methylene or Toluidine blue, ultra-thin slices were stained with an aqueous solution of uranyl acetate and lead citrate.

Peripheral blood comprising heparin was centrifuged for 1 hour at 3,000 rpm. Then 2.5% glutaraldehyde solution was poured on the surface of the film formed for 10-15 minutes. The film was removed, and then treatment proceeded as described above.

Thin slices were observed in the light microscope Polivar (Austria), and semi-thin slices were observed in the electronic microscope JEOL-1200-CX-11 (Japan).

1. Control Studies Prior to Starting of the Chemotherapy and Dicarbamine Administration Patients of Groups I and II.

Hematopoietic cells of different degrees of maturity and differentiation direction are found in puncture biopsies of the bone marrow, a portion of the cells having signs of vacuolization and dystrophy.

There are blast non-differentiated cells of large size with a narrow rim of cytoplasm comprising mainly ribosomes. In these cells, a nucleus of rounded-oval shape with diffuse chromatin and individual nucleoli occupy the main portion of cytoplasm.

A portion of the cells are differentiated in the direction of granulocytic lineage of leukocytes of different type and differentiation degree.

Promyelocytes and myelocytes with rounded-oval nuclei, diffuse chromatin, and cytoplasm comprising different amounts of specific granules are seen. Red blood cells and more mature granulocytes are often situated around these cells.

Accumulations of more differentiated granulocytes, i.e. band neutrophils and segmented neutrophils, are often seen. Specific granules of different types characteristic of neutrophils, eosinophils, and basophils are present in their cytoplasm.

Lymphoid cells of different differentiation degree (small, medium, large-lymphoblastic) are disposed among granulocytes.

Many mature red blood cells, often having different shapes, as well as normoblasts comprising nuclei and platelets are observed.

2. Bone Marrow Following the Chemotherapy with Cyclophosphane and Carboplatin—Group I.

In the preserved hematopoietic cells of different type (granulocytes, lymphocytes, normocytes, red blood cells, platelets), the signs of dystrophy and low degree maturity are observed in the bone marrow puncture biopsies taken after the chemotherapy course.

The cytoplasm of blast cells contains ribosomes and is often vacuolated. Nuclei are large, with diffuse chromatin or accumulations of heterochromatin, occasionally of irregular shape and with sites drawn inside.

The quantity of specific granules in promyelocytes and myelocytes is insignificant, and cytoplasm often has pronounced dystrophic changes.

In the preserved granulocytes of band and segmented types, dystrophic changes and an insignificant amount of specific granules are also observed. The granules present are also often dystrophically modified and vacuolated.

The preserved normoblasts are often of irregular shape with processes and projections of cytoplasm.

It should be noted that in puncture bone marrow biopsies, especially among granulocytes, cells with signs of apoptosis were observed. In such cells, margination of heterochromatin, the signs of nucleus and cytoplasm fragmentation, and formation of apoptotic bodies were noted.

3. Bone Marrow after the Chemotherapy with Cyclophosphane and Carboplatin Along with Dicarbamine Administration—Group II.

In puncture bone marrow biopsies of patients who underwent the chemotherapy along with Dicarbamine administration, hematopoietic cells of different degree and type of differentiation (granulocytes, lymphocytes, platelets, normoblasts) are observed.

The cells of blast type are large, they contain rounded nuclei with diffuse chromatin and individual nucleoli, and their cytoplasm is narrow and contains ribosomes, individual mitochondria and occasionally single primary dense granules are seen.

There are many promyelocytes and myelocytes comprising rounded or oval nuclei with diffuse or condensed chromatin; their cytoplasm comprises a rather big amount of specific granules both primary ones (dark) and less mature ones (more mature).

Band and segmented leukocytes are also frequently observed. The have a concave (bean-like) or segmented nucleus, abundance of specific granules of predominantly neutrophil type in their cytoplasm, less often of eosinophil type with crystalloid structures.

Lymphocytes of different degrees of differentiation contain in their cytoplasm mitochondria, structures of rough endoplasmic reticulum, and occasionally single inclusions in the form of single granules.

Cells of granulocytic type, lymphocytes often form compact accumulations.

Along with red blood cells, normoblasts of different degrees of differentiation and relatively usual shape are observed.

Cells with apoptosis signs are rarely observed.

The same regularities of composition that were earlier described for bone marrow elements were found in studying hematopoietic cells of peripheral blood.

The conducted comparative electronic microscopy of bone marrow and peripheral blood hematopoietic cells in patients with ovarian cancer before and after combined the chemotherapy (Cyclophosphamide+Carboplatin) and during the chemotherapy along with Dicarbamine dosing demonstrated its protective effect from cytotoxic influence of the used preparations.

The study showed that the chemotherapy preparations used in the present work exert a pronounced cytotoxic effect on different types of hematopoietic cells of granulocytic, lymphoid and erythroid lineage.

This cytotoxic effect is expressed in the form of dystrophic changes in the cytoplasm and the death of specific granules that develop in bone marrow cells (and respectively peripheral blood).

Said disorders especially concern granulocytic and, to a lesser extent, lymphoid cells at early stages of their differentiation, i.e. formation of blast cells, promyelocytes, myelocytes, lymphoblasts, and they involve erythroid lineage as well, which results in insufficient accumulation of differentiated functionally competent forms of hematopoietic cells.

Further, as it was found in the elements of granulocytic lineage, the genetically programmed cell death, i.e. apoptosis, is enhanced.

Dystrophic changes and apoptosis generally result in the development of leukopenia, neutropenia, thrombocytopenia and other disorders of hematopoiesis state and limit capabilities of the chemotherapy.

Based on the conducted study, Dicarbamine was demonstrated to protect hematopoietic cells of the bone marrow (and respectively peripheral blood) from the cytotoxic effect of the used the chemotherapy preparations, to promote differentiation of young forms to mature cellular elements, and to reduce the occurrence of apoptosis.

As a result of the found effect of Dicarbamine, in the bone marrow of patients during the chemotherapy accumulation of young (blast) forms of hematopoietic cells occurs and, especially important, their differentiation to functionally competent forms is enhanced.

Thus, under the conditions of the chemotherapy stimulation of the bone marrow hematopoietic cell differentiation, especially of granulocytic lineage cells, and preventing the growth of apoptosis are those mechanisms that underlie the protective effect of Dicarbamine.

EXAMPLE 11

The Efficacy of Dicarbamine in Respect to Reducing Hematological Toxicity of the Chemotherapy in Ovarian Cancer The effect of Dicarbamine was studied in 13 patients with stage III-IV ovarian cancer who underwent 77 courses of the chemotherapy according to the scheme: 400 mg/m$^2$ Carboplatin i.v. drop-wise, once +600 mg/m$^2$ Cyclophosphan i.v. drop-wise, once; the courses were repeated in 28 days. Dicarbamine was prescribed daily at dose 100 mg orally after meals beginning 5 days prior to the first course and then for three weeks. Dosing duration was 26 days, course dose being 2600 mg. Dicarbamine was given again 5 days prior to the second chemotherapy course, and dosing was continued for 21 days. Total duration of Dicarbamine intake during two the chemotherapy courses was 52 days.

Hematological toxicity (leukopenia, neutropenia, thrombocytopenia) was assessed in 13 patients who received 77 courses of the chemotherapy with Dicarbamine as compared with the group of 7 patients who received 25-27 courses of the chemotherapy without Dicarbamine (control).

Hematopoiesis parameters were assessed dynamically many times before and after conducted the chemotherapy (control) as well as dynamically before and after Dicarbamine dosing in the test group. Below hematopoiesis parameters in individual patients who received the chemotherapy according to the indicated scheme with Dicarbamine or without it are presented.

8.1. Patients who Received the Chemotherapy without Dicarbamine 51 year old female, diagnosis: stage III ovarian cancer; she received the first course of the chemotherapy according to therapy scheme as follows: 600 mg/m$^2$ Cyclophosphan and 400 mg/m$^2$ Carboplatin once. Complete blood analysis, course 1 of the chemotherapy

| Parameter, units of measurement | Before course 1 the chemotherapy starting | 5 days after course 1 the chemotherapy | 2 weeks after course 1 the chemotherapy | 3 weeks after course 1 the chemotherapy |
|---|---|---|---|---|
| Leukocytes $10^9/l$ | 4.5 | 3.8 | 2.2 | 2.0 |
| Neutrophils $10^9/l$ | 2.9 | 2.4 | 0.9 | 0.8 |
| Platelets | 168 | 160 | 154 | 150 |

The second course of therapy was delayed by 7 days because of neutropenia.

The second course of the chemotherapy according to therapy scheme was as follows: 600 mg/m² Cyclophosphan+ 400 mg/m² Carboplatin once without Dicarbamine.

Complete blood analysis, course 2 of the chemotherapy

| Parameter, units of measurement | Before course 2 the chemotherapy starting | 5 days after course 2 the chemotherapy | 2 weeks after course 2 the chemotherapy | 3 weeks after course 2 the chemotherapy |
|---|---|---|---|---|
| Leukocytes $10^9/l$ | 3.5 | 3.3 | 2.0 | 2.1 |
| Neutrophils $10^9/l$ | 2.2 | 2.0 | 0.8 | 0.9 |
| Platelets | 178 | 170 | 154 | 150 |

The third course was delayed because of neutropenia.

63 year old female, diagnosis: stage IV ovarian cancer, metastatic involvement of right groin lymph node, ascites; she received the first course of the chemotherapy according to therapy scheme as follows: 600 mg/m² Cyclophosphan+400 mg/m² Carboplatin once, without Dicarbamine.

Complete blood analysis, course 1 of the chemotherapy

| Parameter, units of measurement | Before course 1 of CT starting | 5 days after course 1 of CT | 2 weeks after course 1 of CT | 3 weeks after course 1 of CT |
|---|---|---|---|---|
| Leukocytes $10^9/l$ | 5.0 | 3.9 | 2.1 | 2.0 |
| Neutrophils $10^9/l$ | 3.2 | 1.7 | 0.9 | 1.0 |
| Platelets | 160 | 150 | 151 | 152 |

The second course of therapy was delayed for 4 days because of leuko- and neutropenia.

The second course of the chemotherapy was conducted according to therapy scheme was as follows: 600 mg/m² Cyclophosphan+400 mg/m² Carboplatin once without Dicarbamine.

Complete blood analysis, course 2 of the chemotherapy

| Parameter, units of measurement | Before course 2 of CT starting | 5 days after course 2 of CT | 2 weeks after course 2 of CT | 3 weeks after course 2 of CT |
|---|---|---|---|---|
| Leukocytes $10^9/l$ | 3.7 | 2.9 | 2.0 | 2.2 |
| Neutrophils $10^9/l$ | 2.2 | 1.8 | 0.9 | 0.9 |
| Platelets | 166 | 160 | 140 | 155 |

The third course was delayed because of neutropenia.

8.2. Patients who Received the Chemotherapy Together with Dicarbamine 51 year old female, diagnosis: stage III ovarian cancer; she received the first course of the chemotherapy according to therapy scheme as follows: 600 mg/m² Cyclophosphan and 400 mg/m² Carboplatin at day 1 of therapy. Dicarbamine was prescribed daily at dose 100 mg beginning 5 days prior to course 1 of the chemotherapy and then for 21 days. Period of therapy with Dicarbamine was 26 days before course 2.

Complete blood analysis, course 1 of the chemotherapy with Dicarbamine

| Parameter, units of measurement | Before starting Dicarbamine administration Day "0" | Before starting course 1 of CT Day 5 | After termination of Dicarbamine intake Day 21 | After course 2 of CT Day 33 |
|---|---|---|---|---|
| Leukocytes $10^9/l$ | 5.9 | 5.5 | 4.7 | 4.0 |
| Neutrophils $10^9/l$ | 4.2 | 4.0 | 3.3 | 2.9 |
| Platelets | 170 | 164 | 160 | 158 |

Course 2 of the chemotherapy was conducted in time according to the scheme of therapy as follows: 600 mg/m² Cyclophosphan and 400 mg/m² Carboplatin once at day 28 after first course of the chemotherapy was conducted +Dicarbamine. Dicarbamine was administered at dose 100 mg 5 days prior to course 2 and then daily for 21 days. Total duration of Dicarbamine intake (2 courses of the chemotherapy) was 52 days.

Complete blood Analysis, course 2 of the chemotherapy

| Parameter, units of measurement | Before starting Dicarbamine administration Day 28 after course 1 of CT | Before starting course 1 of CT Day 33 | After termination of Dicarbamine intake Day 54 | Before course 3 of CT Day 61 |
|---|---|---|---|---|
| Leukocytes $10^9/l$ | 4.9 | 5.0 | 4.2 | 4.2 |
| Neutrophils $10^9/l$ | 3.2 | 3.3 | 3.1 | 3.0 |
| Platelets | 180 | 170 | 160 | 160 |

Third course of CT was given in time.

75 year old female, diagnosis: stage III ovarian cancer, ascites; she received the chemotherapy with Dicarbamine according to therapy scheme as follows: 600 mg/m² Cyclophosphan and 400 mg/m² Carboplatin at day 1 of therapy. Dicarbamine was prescribed at dose 100 mg daily beginning 5 days prior to course 1 of CT and then for 21 days. Period of therapy with Dicarbamine was 26 days before course 2.

Complete blood analysis, course 1 of the chemotherapy with Dicarbamine

| Parameter, units of measurement | Before starting Dicarbamine administration Day "0" | Before starting course 1 of CT Day 5 | After termination of Dicarbamine intake Day 21 | Before course 2 of CT Day 33 |
|---|---|---|---|---|
| Leukocytes $10^9/l$ | 7.4 | 7.2 | 6.6 | 5.2 |
| Neutrophils $10^9/l$ | 5.7 | 5.0 | 5.2 | 3.8 |
| Platelets | 174 | 165 | 162 | 167 |

Course 2 of the chemotherapy was conducted in time according to the scheme of therapy as follows: 600 mg/m² Cyclophosphan and 400 mg/m² Carboplatin once at day 28 after the first course of the chemotherapy was conducted +Dicarbamine. Dicarbamine was administered at dose 100 mg 5 days prior to course 2 and then daily for 21 days. Total duration of Dicarbamine intake (2 courses of the chemotherapy) was 52 days.

Complete blood analysis, course 2 of the chemotherapy

| Parameter, units of measurement | Before starting Dicarbamine administration Day 28 after course 1 of CT | Before starting course 1 of CT Day 33 | After termination of Dicarbamine intake Day 54 | Before course 3 of CT Day 61 |
|---|---|---|---|---|
| Leukocytes 10⁹/l | 7.8 | 8.2 | 7.6 | 7.2 |
| Neutrophils 10⁹/l | 5.2 | 6.0 | 6.2 | 5.8 |
| Platelets | 165 | 160 | 162 | 157 |

The third course of CT was given at term.

65 year old female, diagnosis: stage 1V ovarian cancer, ascites, metastatic involvement of the umbilical region; she received the chemotherapy with Dicarbamine according to therapy scheme as follows: 600 mg/m² Cyclophosphan and 400 mg/m² Carboplatin at day 1 of therapy. Dicarbamine was prescribed at dose 100 mg daily beginning 5 days prior to course 1 of CT and then for 21 days. Period of therapy with Dicarbamine was 26 days before course 2.

Complete blood analysis, course 1 of the chemotherapy with Dicarbamine

| Parameter, units of measurement | Before starting Dicarbamine administration Day "0" | Before starting course 1 of CT Day 5 | After termination of Dicarbamine intake Day 21 | Before course 2 of CT Day 33 |
|---|---|---|---|---|
| Leukocytes 10⁹/l | 6.6 | 5.9 | 5.5 | 5.0 |
| Neutrophils 10⁹/l | 5.0 | 4.2 | 4.4 | 3.4 |
| Platelets | 170 | 172 | 166 | 164 |

Course 2 of the chemotherapy was conducted in time according to the scheme of therapy as follows: 600 mg/m² Cyclophosphan and 400 mg/m² Carboplatin once at day 28 after the first course of the chemotherapy was conducted +Dicarbamine. Dicarbamine was administered at dose 100 mg 5 days prior to course 2 and then daily for 21 days. Total duration of Dicarbamine intake (2 courses of the chemotherapy) was 52 days.

Complete blood analysis, course 2 of the chemotherapy

| Parameter, units of measurement | Before starting Dicarbamine administration Day 28 after course 1 of CT | Before starting course 1 of CT Day 33 | After termination of Dicarbamine intake Day 54 | Before course 3 of CT Day 61 |
|---|---|---|---|---|
| Leukocytes 10⁹/l | 5.6 | 5.8 | 5.7 | 5.5 |
| Neutrophils 10⁹/l | 3.0 | 3.2 | 3.4 | 3.2 |
| Platelets | 170 | 170 | 176 | 165 |

The third course of CT was given at term.

8.3. Comparative Data on Hematological Toxicity in Patients who Received the Chemotherapy and Those who Received or not Received Dicarbamine are Shown in Tables 16 and 17.

TABLE 16

Number (%) of patients with hematological toxicity who received the chemotherapy without Dicarbamine

| Type of toxicity | Number of CT courses | Degree of hematological toxicity according to WHO | | | | | |
|---|---|---|---|---|---|---|---|
| | | 0 | I | II | III | IV | III + IV |
| Leukopenia | 26 | 3 | 5 | 12 | 5 | 1 | 6 |
| | | 11.5% | 19.2% | 46.1% | 19.2% | 3.8% | 23.07% |
| Neutropenia | 26 | 7 | 0 | 8 | 6 | 5 | 11 |
| | | 26.9% | | 30.7% | 23.07% | 19.2% | 42.3% |
| Thrombocytopenia | 25 | 10 | 3 | 7 | 4 | 1 | 5 |
| | | 40.0% | 12.0% | 28.0% | 16.0% | 4.0% | 20.0% |

TABLE 17

Number (%) of patients with hematological toxicity who received the chemotherapy with Dicarbamine

| Type of toxicity | Number of CT courses | Degree of hematological toxicity according to WHO | | | | | |
|---|---|---|---|---|---|---|---|
| | | 0 | I | II | III | IV | III + IV |
| Leukopenia | 77 | 6 | 18 | 43 | 10 | 0 | 10 |
| | 100% | 7.7% | 23.3% | 55.8% | 12.9% | | 12.9% |
| Neutropenia | 67 | 21 | 12 | 23 | 5 | 6 | 11 |
| | 100% | 31.3% | 17.9% | 34.3% | 7.4% | 8.9% | 16.4% |
| Thrombocytopenia | 76 | 27 | 32 | 10 | 6 | 1 | 7 |
| | 100% | 35.5% | 42.1% | 13.1% | 7.8% | 1.3% | 9.1% |

The data obtained show that the limiting hematological toxicity of stage III-IV without use of Dicarbamine (table 16) achieves on the basis of leukopenia over 23.0%, on the basis of neutropenia 42.3% and by thrombocytopenia 20.0%.

In the group of patients who received Dicarbamine the occurrence rate of leuko-, neutro- and thrombocytopenia was significantly lower (Table 17). Hematological toxicity on the basis of leukopenia decreased to 12.9%, i.e. 1.8-fold, on the basis of neutropenia 2.6-fold and on the basis of thrombocytopenia 2.2-fold. Thus, the use Dicarbamine resulted in reducing all the listed kinds of hematological toxicity.

Below the data are presented supporting the fact that administration of Dicarbamine does not lower therapy efficacy with cytostatic agents but on the contrary enhances to some extent the effect achieved.

Efficacy of therapy was assessed in groups of patients following two courses of the chemotherapy with or without Dicarbamine according to the above described scheme. Efficacy was assessed according to the generally accepted parameters: CR—complete remission, PR—partial remission, SB—stabilization; and Progr. —progression.

The data obtained are presented in Table 18.

TABLE 18

Efficacy of treating patients according to scheme Cyclophosphane + Carboplatin with Dicarbamine

| Groups of patients | Number of patients | CR | PR | SB | Progr. |
|---|---|---|---|---|---|
| The chemotherapy | 6 | 2 | 1 | 2 | 1 |
| | 100.0% | 33.3% | 16.6% | 33.5% | 16.6% |
| The chemotherapy + Dicarbamine | 15 | 4 | 7 | 2 | 2 |
| | 100.0% | 26.6% | 46.6% | 13.5% | 13.3% |

The data presented show that in the group of patients who received the chemotherapy without Dicarbamine, tumor growth control (CR+PR) amounts to 49.9%. In the group of patients who received the chemotherapy with Dicarbamine efficacy of therapy is 73.2%.

Thus, the use of Dicarbamine in treating patients who receive the chemotherapy results in reducing main kinds of hematological toxicity without decrease in the efficacy of therapy.

The test and clinical data presented above evidently prove the efficacy of peptide derivatives of general formula (I) as non-specific inducers of differentiation which, when using peptide derivatives together with myelosuppressive the chemotherapy, reduce the degree and number of neutropenias and in use alone results in growth stabilization of murine hemoblastosis, of differentiating murine and human melanoma including the case of absent efficacy of the chemotherapy.

The effect of peptide derivatives of general formula (I) on tumor growth was shown to be associated with delay of proliferation activity of tumor cells and an increased degree of differentiation, in particular melanin synthesizing capability of melanoma cells and differentiation induction of Friend erythroblastosis precursor cells.

Clinical investigations revealed the properties of peptide derivatives of general formula (I) to significantly lower hematological toxicity in treating cancer patients using different schemes of combined the chemotherapy. Thus, when treating patients suffering from ovarian cancer with platinum preparations (Cyclophosphane) along with peptide derivatives, the degree of limiting neutropenia and thrombocytopenia decreased 2-3-fold. At the same time, the efficacy of therapy was not decreased.

TABLE 4

The effect of Dicarbamine on M-6 human melanoma growth in nude mice

| Day after inoculation | Control n = 7 M + m* | | Dicarbamine 1.5 mg/kg n = 10 M + m | | | Dicarbamine 4.5 mg/kg n = 10 M + m | | |
|---|---|---|---|---|---|---|---|---|
| | V | % | V | % | p** | V | % | P |
| 18 day | 66.2 + 2.8 | 100 | 21.8 + 12.8 | 100 | | 91.9 + 54.4 | 100 | |
| 25 day | 266.0 + 69.4 | 329.0 + 88.9 | 77.5 + 46.4 | 302.0 + 186.0 | 0.82 | 266.0 + 198.0 | 166.0 + 93.0 | 0.015 |
| 33 day | 582.0 + 127.4 | 132.9 + 57.3 | 342.0 + 142.0 | 428.0 + 313.1 | 0.11 | 852.0 + 495.0 | 276.0 + 104.0 | 0.011 |
| 39 day | 701.0 + 123.5 | 21.9 + 12.6 | 435.0 + 187.0 | 23.2 + 22.1 | 0.92 | 1129.0 + 600.0 | 39.8 + 27.3 | 0.169 |
| 46 day | 778.0 + 148.4 | 10.5 + 8.1 | 662.0 + 417.0 | 23.9 + 31.0 | 0.45 | 1354.0 + 735.0 | 19.6 + 17.5 | 0.276 |
| 53 day | 821.0 + 221.8 | 3.8 + 10.3 | 783.0 + 423.0 | 18.6 + 54.0 | 0.43 | 1550.0 + 780.0 | 4.2 + 22.5 | 0.538 |

*average value with standard deviation,
**significance calculation was done only for the data of percent change in tumor volume

TABLE 12

Dynamics of mice peripheral blood leukocytes formula under Cyclophosphamide effect in combination with Dicarbamine

| Formed elements | Days post Cyclophosphamide administration | | | | | | |
|---|---|---|---|---|---|---|---|
| | 3 | 5 | 7 | 10 | 13 | 17 | 21 |
| Group 1 | | | | | | | |
| Myelocytes | 0 | 0 | 0.4/54 ± 0.4 | 0 | 0 | 0 | 0 |
| Young | 0 | 0 | 1.4/188 ± 148 | 0.4/48 ± 3 | 0 | 0 | 0 |
| Band | 3.2/89 ± 16 | 4.6/370 ± 13 | 4.8/660 ± 223 | 5.7/620 ± 260 | 2.2/293 ± 146 | 1.6/198 ± 150 | 2.7/286 ± 214 |
| Segmented | 10.4/290 ± 210 | 17.6/1400± | 31.4/4200 ± 960 | 27/3200 ± 450 | 24/3190 + 440 | 19.6/2430 ± 545 | 18.8/2444 ± 585 |
| Eosinophils | 1.2/34 ± 15 | 1.2/95.5 ± 44 | 0 | 0 | 1.2/290 ± 73 | 2.6/322 ± 93 | 1.4/182 ± 72 |
| Monocytes | 6.2/172 ± 62 | 7.2/570 ± 17 | 5.4/724 ± 74 | 5.2/690 ± 130 | 4.6/612 ± 219 | 5.4/60 ± 150 | 4.0/520 ± 143 |
| Lymphocytes | 75.6/2120 ± 310 | 69.4/5520± | 56.2/7530 ± 1250 | 65.4/7780 ± 450 | 67.8/9017 ± 580 | 70.8/8780 ± 545 | 73.8/9594 ± 585 |
| Group 2 | | | | | | | |
| Myelocytes | 0 | 0.6/26 ± 5 | 0 | 0 | 0 | 0 | 0 |
| Young | 0.4/4 ± 1 | 1.6/70 ± 24 | 0.6/63 ± 12 | 0.4/26 ± 5 | 0 | 0 | 0 |
| Band | 1.2/13 ± 3 | 4.2/184 ± 48 | 3.6/378 ± 41 | 3.2/206 ± 71 | 2.2/2681134 | 1.6/195 ± 67 | 1.4/167 ± 67 |
| Segmented | 5.2/55 ± 0.6 | 16/700 ± 240 | 35.2/3700 ± 705 | 23.7/1494 ± 390 | 18.2/2220 ± 470 | 20.2/2460 ± 37 | 19.6/2330 ± 714 |
| Eosinophils | 0.4/4 ± 1 | 0.4/17 ± 5 | 0 | 1.0/64 ± 35 | 1.4/170 ± 134 | 1.4/170 ± 79 | 1.6/190 ± 130 |
| Monocytes | 4.649 ± 17.5 | 6.4/280 ± 48 | 4.8/504 ± 115 | 5.4/350 ± 160 | 3.8/464 ± 134 | 4.4/537 ± 134 | 4.6/547 ± 65 |
| Lymphocytes | 88.2/935 ± 23 | 71/3110 ± 217 | 55.8/6860 ± 750 | 65.8/4240 ± 708 | 75.0/9150 ± 402 | 71.6/8740 ± 604 | 71.6/8520 ± 785 |

Table presents %/absolute amount in mm$^3$

TABLE 13

Cellularity* of murine bone marrow under effect of Cyclophosphamide and Cyclophosphamide in combination with Dicarbamine

| Group No | Days after Cyclophosphamide administration | | | | | | |
|---|---|---|---|---|---|---|---|
| | 3 | 5 | 7 | 10 | 13 | 17 | 21 |
| 1 | 14.5 ± 3.43 | 21.55 ± 1.92 | 32.35 ± 3.57 | 33.8 ± 3.85 | 32.6 ± 5.22 | 28.25 ± 3.02 | 30.4 ± 2.75 |
| 2 | 8.2 ± 1.65 | 13.05 ± 2.75 | 25.22 ± 2.75 | 27.9 ± 2.75 | 30.15 ± 6.6 | 25.0 ± 3.16 | 26.55 ± 4.53 |

*number of cells in millions

TABLE 14

The effect of peptide derivatives on tumor size in mice with Friend erythroblastosis

| Compound | Single dose (mg/kg) in daily dosing for 5 days | Average tumor volumes at days after termination of therapy | | | Tumor growth inhibition, % | | |
|---|---|---|---|---|---|---|---|
| | | 8 | 13 | 19 | | | |
| Control | — | 342[139 ÷ 545] | 706[457 ÷ 961] | 777[199 ÷ 1355] | | | |
| 1 | 1.5 | 157[73 ÷ 241] | 284[197 ÷ 371] | 318[136 ÷ 500] | 54 | 60* | 63 |
| 2 | 1.5 | 130[68 ÷ 192] | 367[105 ÷ 629] | 367[105 ÷ 629] | 62 | 48 | 57 |
| Control** | — | 249[150 ÷ 348] | 678[373 ÷ 983] | 645[385 ÷ 905] | — | — | — |
| 3 | 1.5** | 77[52 ÷ 102] | 219[104 ÷ 334] | 368[193 ÷ 543] | 69* | 68* | 43 |
| Dicarbamine | 1.5 | 96[37 ÷ 155] | 150[87 ÷ 213] | 290[103 ÷ 477] | 61 | 78* | 55 |
| | 4.5** | 129[67 ÷ 191] | 300[130 ÷ 470] | 485[1354 ÷ 835] | 62 | 58 | 38 |

Notes:
*difference from the control is significant at p < 0.05
**the second test

TABLE 15

The effect of peptide derivatives on tumor growth rate in mice with Friend erythroblastosis

| Compound | Single dose (mg/kg), daily dosing for 5 days | Relative tumor volumes at days after tumor inoculation along with daily Dicarbamine intake $V_i/V_1$ | | | Tumor growth inhibition, % | | |
|---|---|---|---|---|---|---|---|
| | | 8 | 13 | 19 | | | |
| Control | — | 1.0 | 2.0 | 2.3 | | | |
| 1 | 1.5 | 1.0 | 1.8 | 2.0 | 54 | 60** | 63 |
| 2 | 1.5 | 1.0 | 2.8 | 2.8 | 62 | 48 | 57 |
| Control*** | 1.5 | 1.0 | 2.72 | 2.59 | — | — | — |
| 3 | 1.5*** | 1.0 | 2.8 | 4.78 | 69** | 68** | 43 |
| Dicarbamine | 1.5 | 1.0 | 1.56 | 3.0 | 61 | 78** | 55 |
| | 4.5*** | 1.0 | 2.3 | 3.76 | 62 | 58 | 38 |

Notes:
*p < 0.05
**the second test

The invention claimed is:

1. A method for treatment of melanoma or hemoblastosis in mammals including humans, which method comprises administration of an effective amount of a peptide derivative of general formula (I)

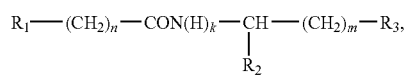

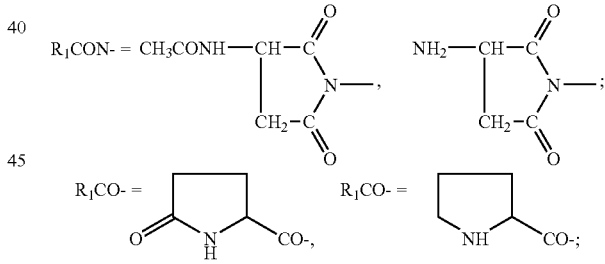

wherein:
$R_1$ is
- (a) a $C_1$-$C_3$ hydrocarbon radical substituted by a functional group selected from an amino, a $C_1$-$C_5$ amido-, and a carboxylic group, the carboxylic group being optionally esterified; or
- (b) a $C_1$-$C_3$ hydrocarbon radical simultaneously substituted by an amino group which is optionally substituted by an acyl substituent; or
- (c) a $C_1$-$C_3$ hydrocarbon radical substituted by a 5-6 membered unsaturated heterocyclic group, wherein the hydrocarbon radical can simultaneously comprise an amino group optionally substituted by an acyl substituent; or
- (d) a saturated heterocyclic group; or
- (e) when n is 0 and k is 0, $R_2$ is a hydrogen atom or a carboxyl group that can be esterified;
$R_3$ is:
- (a) a 5-6 membered saturated or unsaturated cyclic or heterocyclic group, or
- (b) a amino group; or
- (c) a carboxyl group which is optionally esterified;

n=0-4
m=1-4, and
k=0-1;
or pharmaceutically acceptable salts thereof.

2. The method of claim 1, wherein the peptide derivative of general formula (I) is administered daily orally at dose 0.5-5.0 mg/kg.

3. The method of claim 1, wherein the peptide derivative of general formula (I) is administered in combination with a course of chemotherapy.

4. The method of claim 1, wherein in order to stabilize growth of melanoma or hemoblastosis the peptide derivative of general formula (I) is administered for at least 15 days.

5. The method of claim 1, wherein in order to enhance the efficacy of immunotherapy of melanoma or hemoblastosis the peptide derivative of general formula (I) is administered together with interferon.

6. The method of claim 1, wherein in order to lower hematological toxicity the peptide derivative of general formula (I) is administered 5 days before starting a chemotherapy course and up to its termination.

7. A method for treatment of melanoma or hemoblastosis in mammals including humans, which method comprises administration of an effective amount of a peptide derivative having the structural formula $$\text{imidazole-CH}_2\text{CH}_2\text{NHCO(CH}_2)_3\text{COOH}.$$

8. A method for reducing neutropenia comprising administration of an effective amount of a peptide derivative of general formula $$R_1\text{---}(CH_2)_n\text{---}CON(H)_k\text{---}\underset{R_2}{CH}\text{---}(CH_2)_m\text{---}R_3, \quad (I)$$

wherein:

$R_1$ is
- (a) a $C_1$-$C_3$ hydrocarbon radical substituted by a functional group selected from an amino, a $C_1$-$C_5$ amido-, and a carboxylic group, the carboxylic group being optionally esterified; or
- (b) a $C_1$-$C_3$ hydrocarbon radical simultaneously substituted by an amino group which is optionally substituted by an acyl substituent; or
- (c) a $C_1$-$C_3$ hydrocarbon radical substituted by a 5-6-membered unsaturated heterocyclic group, wherein the hydrocarbon radical can simultaneously comprise an amino group optionally substituted by acyl substituent; or
- (d) a saturated heterocyclic group; or
- (e) when n is 0 and k is 0, $R_1CON\text{-} = CH_3CONH\text{---}CH\text{---}C(=O)\text{---}N\text{---}CH_2\text{---}C(=O)$,  $NH_2\text{---}CH\text{---}C(=O)\text{---}N\text{---}CH_2\text{---}C(=O)$;

$R_1CO\text{-} =$ (5-oxopyrrolidin-2-yl-carbonyl),  $R_1CO\text{-} =$ (pyrrolidin-2-yl-carbonyl);

$R_2$ is a hydrogen atom or a carboxyl group that can be esterified;

$R_3$ is
- (a) a 5-6-membered saturated or unsaturated cyclic or heterocyclic group, or
- (b) an amino- or carboxyl group; or
- (c) a carboxyl group which is optionally esterified;

n=0-4,
m=1-4,
k=0-1;

or pharmaceutically acceptable salts thereof.

9. The method according to claim 8, wherein the peptide derivative of general formula (I) is administered orally at a daily dose of 0.5-5.0 mg/kg.

10. The method according claim 8, wherein the peptide derivative of general formula (I) is administered in combination with a course of chemotherapy.

11. The method according to claim 8, wherein in order to lower neutropenia the peptide derivative of general formula (I) is administered 5 days before starting a chemotherapy course and up to its termination.

12. The method according to claim 8, wherein:

$R_1$ is $NH_2CH_2\text{---}$, $HOOC\text{---}CH_2\text{---}$, $CH_3CONH\text{---}CH_2\text{---}$, $CH_3OCO\text{---}CH_2\text{---}$, $NH_2\text{---}\underset{COOH}{CH}\text{---}$,  $NH_2\text{---}\underset{CH_2\text{---}CH_2\text{---}COOH}{CH}\text{---}$, $CH_3\text{---}CONH\text{---}\underset{CH_2\text{---}COOH}{CH}\text{---}$,  $CH_3CO\text{---}NH\text{---}\underset{COOH}{CH}\text{---}$, $NH_2\text{---}\underset{CH_2\text{-4Im}}{CH}\text{---}$;

$R_1CON\text{---} = CH_3CONH\text{---}CH\text{---}C(=O)\text{---}N\text{---}CH_2\text{---}C(=O)$, $NH_2\text{---}CH\text{---}C(=O)\text{---}N\text{---}CH_2\text{---}C(=O)$, $R_1CO\text{---} =$ (5-oxopyrrolidin-2-yl-carbonyl), $R_1CO\text{---} =$ (pyrrolidin-2-yl-carbonyl), n = 0-4; k = 0-1   $R_2$ = H, COOH, COOCH$_3$, $R_3$ = imidazolyl, indolyl, phenyl, pyridyl, morpholinyl, $NH_2$, COOH, ---COOCH$_3$, m = 1-4.

13. A method for reducing neutropenia comprising administration of an effective amount of a peptide derivative having the formula

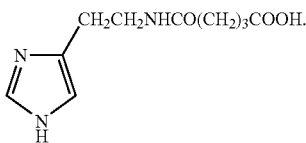

14. A method for enhancing efficacy of immunotherapy of malignant tumors selected from melanoma or hemoblastosis, comprising administration of interferon in combination with a peptide derivative which is

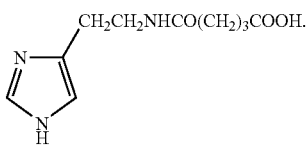

15. The method according to claim 1, wherein:

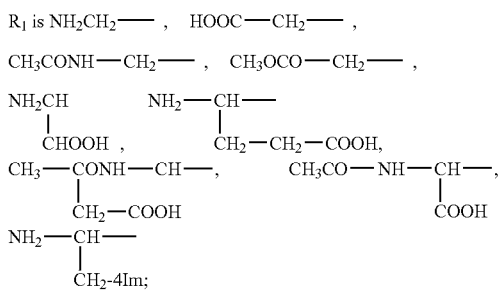

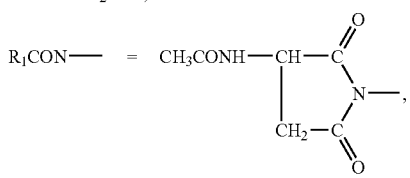

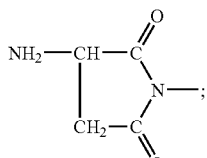

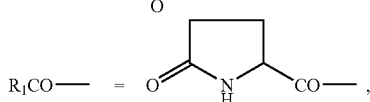

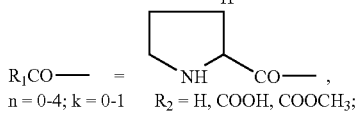

n = 0-4; k = 0-1    $R_2$ = H, COOH, COOCH$_3$;

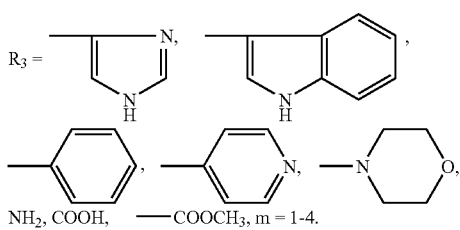

$NH_2$, COOH,  —COOCH$_3$, m = 1-4.

16. A method for reducing a side effect of a cytostatic agent in mammals including humans, wherein the side effect is selected from neutropenia or thrombocytopenia, comprising administering an effective amount of a peptide derivative of general formula

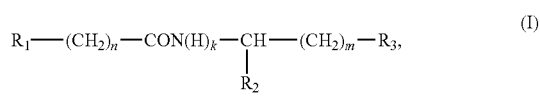

(I)

wherein:
$R_1$ is
(a) a $C_1$-$C_3$ hydrocarbon radical substituted by a functional group selected from an amino, a $C_1$-$C_5$ amido-, and a carboxylic group, the carboxylic group being optionally esterified; or
(b) a $C_1$-$C_3$ hydrocarbon radical simultaneously substituted by an amino group which is optionally substituted by an acyl substituent; or
(c) a $C_1$-$C_3$ hydrocarbon radical substituted by a 5-6-membered unsaturated heterocyclic group, wherein the hydrocarbon radical can simultaneously comprise an amino group optionally substituted by acyl substituent; or
(d) a saturated heterocyclic group; or
(e) when n is 0 and k is 0,

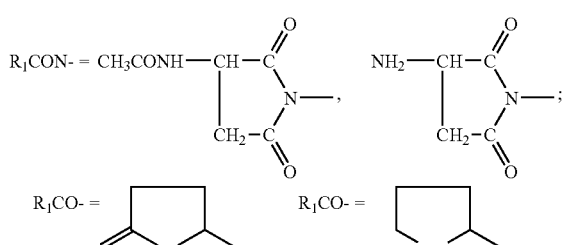

$R_2$ is a hydrogen atom or a carboxyl group that can be esterified;
$R_3$ is
(d) a 5-6-membered saturated or unsaturated cyclic or heterocyclic group, or
(e) an amino- or carboxyl group; or
(f) a carboxyl group which is optionally esterified;
n=0-4,
m=1-4,
k=0-1;
or pharmaceutically acceptable salts thereof.

17. A method for reducing a side effect of a cytostatic agent in mammals including humans, wherein the side effect is selected from neutropenia or thrombocytopenia, comprising administering an effective amount of a peptide derivative having the formula

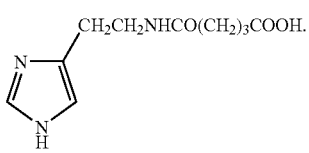

18. The method of claim 16 wherein the side effect is neutropenia.

19. The method of claim 16 wherein the side effect is thrombocytopenia.

20. A peptide derivative of general formula (I)

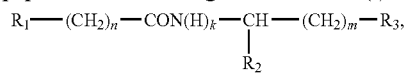

wherein:

(a) $R_1$ is

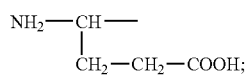

n is 0; k is 1; $R_2$ is H; m is 1; and $R_3$ is

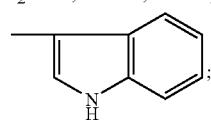

(b) $R_1$ is $NH_2$—$CH_2$—; n is 2; k is 1; $R_2$ is —COOH; m is 1; and $R_3$ is

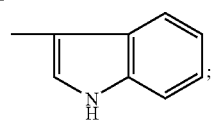

(c) $R_1$ is $NH_2$—$CH_2$—; n is 2; k is 1; $R_2$ is H; m is 1; and $R_3$ is —$C_6H_5$;

(d) $R_1$ is $NH_2$—$CH_2$—; n is 2; k is 1; $R_2$ is H; m is 1; and $R_3$ is

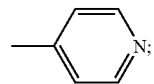

(e) $R_1$ is HOOC—$CH_2$—; n is 2; k is 1; $R_2$ is —COOH; m is 4; and $R_3$ is —$NH_2$; or (f) $R_1$ is

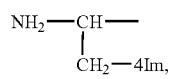

wherein 4Im is

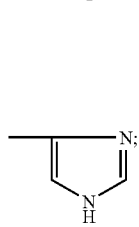

n is 0; k is 1; $R_2$ is H; m is 1; and $R_3$ is —$COOCH_3$.

* * * * *

UNITED STATES PATENT AND TRADEMARK OFFICE
CERTIFICATE OF CORRECTION

PATENT NO.       : 7,759,313 B2                                                     Page 1 of 1
APPLICATION NO.  : 10/505976
DATED            : July 20, 2010
INVENTOR(S)      : Nebolsin et al.

It is certified that error appears in the above-identified patent and that said Letters Patent is hereby corrected as shown below:

Column 40, line 29:

" 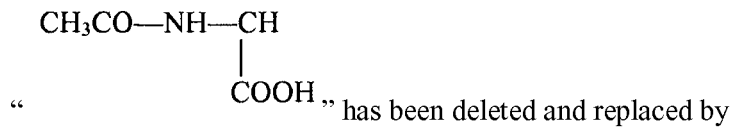 " has been deleted and replaced by

-- 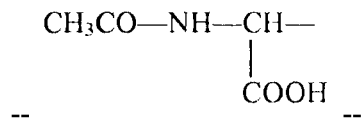 --

Column 41, line 30:

" 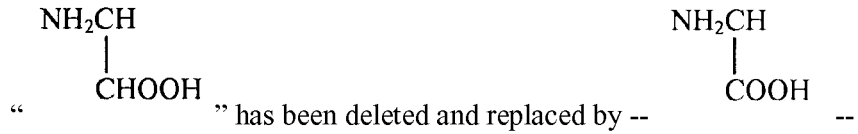 " has been deleted and replaced by -- 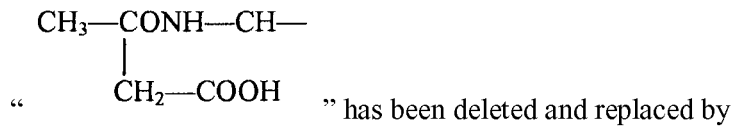 --

Column 41, line 31:

" 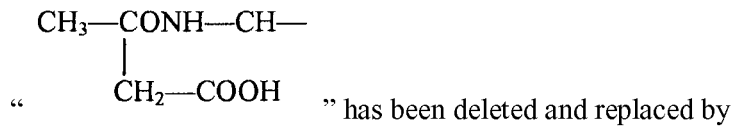 " has been deleted and replaced by

-- 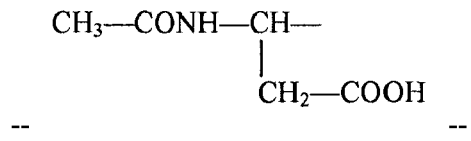 --

Signed and Sealed this

Fifth Day of October, 2010

David J. Kappos
*Director of the United States Patent and Trademark Office*